(12) United States Patent
Wyeth et al.

(10) Patent No.: US 11,865,243 B2
(45) Date of Patent: Jan. 9, 2024

(54) PARAMETER MONITORING IN MEDICAL TREATMENT SYSTEMS

(71) Applicant: NxStage Medical, Inc., Lawrence, MA (US)

(72) Inventors: Mark T. Wyeth, Andover, MA (US); Robert Paul McCarty, Reading, MA (US); Gregory Yantz, Boxford, MA (US); James Ian Johnson, Charlestown, MA (US); Joseph E. Turk, Jr., North Andover, MA (US); James M. Brugger, Newburyport, MA (US); Jeffrey H. Burbank, Boxford, MA (US)

(73) Assignee: NxStage Medical, Inc., Lawrence, MA (US)

( * ) Notice: Subject to any disclaimer, the term of this patent is extended or adjusted under 35 U.S.C. 154(b) by 984 days.

(21) Appl. No.: 16/328,443

(22) PCT Filed: Aug. 30, 2017

(86) PCT No.: PCT/US2017/049489
§ 371 (c)(1),
(2) Date: Feb. 26, 2019

(87) PCT Pub. No.: WO2018/045102
PCT Pub. Date: Mar. 8, 2018

(65) Prior Publication Data
US 2020/0206405 A1 Jul. 2, 2020

Related U.S. Application Data

(60) Provisional application No. 62/381,413, filed on Aug. 30, 2016.

(51) Int. Cl.
*A61M 1/36* (2006.01)
*A61M 1/16* (2006.01)

(52) U.S. Cl.
CPC ........ *A61M 1/3639* (2013.01); *A61M 1/1611* (2014.02); *A61M 1/1621* (2014.02);
(Continued)

(58) Field of Classification Search
CPC ....... A61B 5/01; A61B 5/02035; A61B 5/021; A61B 5/024; A61B 5/0533; A61B 5/1118;
(Continued)

(56) References Cited

U.S. PATENT DOCUMENTS 3,659,511 A * 5/1972 Nerwin ................. G03B 17/52
396/365
4,009,078 A 2/1977 Wilkins et al.
(Continued)

FOREIGN PATENT DOCUMENTS

CN 102466680 A 5/2012
EP 2163271 B1 3/2010
(Continued)

OTHER PUBLICATIONS

IBM Lookup Table Definition (Year: 2021).*
(Continued)

*Primary Examiner* — Patrick Orme
(74) *Attorney, Agent, or Firm* — Potomac Law Group, PLLC

(57) ABSTRACT

A blood treatment system with pressure sensors may be configured to control blood flow to and from the patient and use readings of the pressure sensors to determine a change in a pressure drop across a flow restriction in the blood circuit to estimate a condition of the machine or the patient, or outputting data responsive to the estimation. Further embodiments employ measurement of pressure drop to detect abnormal viscosity or viscosity variations in order to detect possible infection.

23 Claims, 5 Drawing Sheets

(52) U.S. Cl.
CPC ... *A61M 1/3623* (2022.05); *A61M 2205/3344* (2013.01); *A61M 2205/52* (2013.01); *A61M 2230/207* (2013.01)

(58) Field of Classification Search
CPC ............ A61B 5/14542; A61M 1/1601; A61M 1/1605; A61M 1/1611; A61M 1/1621; A61M 1/1647; A61M 1/3639; A61M 2205/3331; A61M 2205/3344; A61M 2205/52; A61M 2230/207; A61M 2230/208; A61M 2230/63
See application file for complete search history.

(56) References Cited

U.S. PATENT DOCUMENTS

| | | | |
|---|---|---|---|
| 5,306,229 A * | 4/1994 | Brandt | A61F 13/066 602/61 |
| 5,375,604 A * | 12/1994 | Kelly | A61B 5/332 600/483 |
| 5,591,399 A | 1/1997 | Goldman et al. | |
| 5,693,008 A * | 12/1997 | Brugger | A61M 1/3639 604/4.01 |
| 5,837,905 A | 11/1998 | Strauss et al. | |
| 5,841,737 A * | 11/1998 | Schaefer | G01V 1/157 367/147 |
| 5,928,179 A | 7/1999 | Plotkin | |
| 6,217,539 B1 | 4/2001 | Goldau | |
| 6,221,672 B1 | 4/2001 | Baugh et al. | |
| 6,322,524 B1 * | 11/2001 | Kensey | A61B 5/02035 600/573 |
| 6,526,357 B1 * | 2/2003 | Soussan | A61M 1/3496 702/45 |
| 7,131,389 B1 * | 11/2006 | Hawkes | B63G 8/18 114/330 |
| 7,341,568 B2 | 3/2008 | Zhang | |
| 7,699,992 B2 | 4/2010 | Sternby | |
| 7,727,222 B2 | 6/2010 | Silva et al. | |
| 7,931,610 B2 | 4/2011 | Murakami et al. | |
| 8,012,114 B2 | 9/2011 | Daniel et al. | |
| 8,060,190 B2 | 11/2011 | Sommo et al. | |
| 8,086,323 B2 | 12/2011 | Reghabi et al. | |
| 8,182,692 B2 | 5/2012 | Gotch | |
| 8,209,033 B2 | 6/2012 | Zhang et al. | |
| 8,216,478 B2 | 7/2012 | Noack et al. | |
| 8,239,010 B2 | 8/2012 | Banet et al. | |
| 8,246,546 B2 | 8/2012 | Huiku | |
| 8,246,567 B2 | 8/2012 | Bene | |
| 8,287,739 B2 | 10/2012 | Barrett et al. | |
| 8,361,006 B2 | 1/2013 | Kraemer | |
| 8,524,154 B2 | 9/2013 | Shekalim et al. | |
| 8,529,767 B2 | 9/2013 | Zhang | |
| 8,583,226 B2 | 11/2013 | Moissl et al. | |
| 8,591,865 B2 | 11/2013 | Wang et al. | |
| 8,613,705 B2 | 12/2013 | Scheurer et al. | |
| 8,632,485 B2 | 1/2014 | Schlaeper et al. | |
| 8,663,931 B2 | 3/2014 | Saito et al. | |
| 8,792,089 B2 | 7/2014 | Zhang et al. | |
| 8,858,486 B2 | 10/2014 | Zhang et al. | |
| 8,900,172 B2 | 12/2014 | Pohlmeier | |
| 8,960,010 B1 * | 2/2015 | Crnkovich | A61M 1/34 73/714 |
| 9,037,207 B2 | 5/2015 | Al-Ali et al. | |
| 9,144,639 B2 | 9/2015 | Vantard et al. | |
| 9,220,827 B2 | 12/2015 | Meibaum et al. | |
| 9,278,171 B2 | 3/2016 | Brandl et al. | |
| 9,381,289 B2 | 7/2016 | Hedmann et al. | |
| 9,423,338 B2 | 8/2016 | Alic et al. | |
| 9,566,377 B2 | 2/2017 | Jones et al. | |
| 9,610,393 B2 | 4/2017 | Rada et al. | |
| 9,724,455 B2 | 8/2017 | Kopperschmidt et al. | |
| 9,743,843 B2 | 8/2017 | Chamney et al. | |
| 9,743,868 B2 | 8/2017 | Ballam et al. | |
| 9,795,739 B2 | 10/2017 | Al-Ali et al. | |
| 9,814,412 B2 | 11/2017 | Zhang et al. | |
| 9,861,733 B2 | 1/2018 | Burbank et al. | |
| 9,907,897 B2 | 3/2018 | Burbank et al. | |
| 9,943,633 B2 | 4/2018 | Sigg et al. | |
| 9,968,298 B2 | 5/2018 | Heppe et al. | |
| 9,980,663 B2 | 5/2018 | Wabel et al. | |
| 9,987,406 B2 | 6/2018 | Wright et al. | |
| 10,001,454 B2 | 6/2018 | Schick et al. | |
| 10,010,289 B2 | 7/2018 | Gagel et al. | |
| 10,016,549 B2 | 7/2018 | Stonger et al. | |
| 10,092,249 B2 | 10/2018 | Kiani et al. | |
| 10,117,590 B2 | 11/2018 | Barrett et al. | |
| 10,155,077 B2 | 12/2018 | Maierhofer et al. | |
| 2003/0113933 A1 | 6/2003 | Jansson et al. | |
| 2004/0247401 A1 * | 12/2004 | Witheridge | B65D 88/72 406/122 |
| 2007/0215545 A1 * | 9/2007 | Bissler | A61M 1/1613 210/646 |
| 2009/0008331 A1 * | 1/2009 | Wilt | A61M 1/3424 210/321.71 |
| 2009/0078622 A1 | 3/2009 | Zhang et al. | |
| 2009/0095679 A1 * | 4/2009 | Demers | A61M 1/1613 210/101 |
| 2010/0028208 A1 * | 2/2010 | Shekalim | A61B 5/14532 422/68.1 |
| 2010/0099958 A1 | 4/2010 | Kotanko et al. | |
| 2010/0112583 A1 | 5/2010 | Ichiishi et al. | |
| 2010/0137693 A1 | 6/2010 | Porras et al. | |
| 2010/0191164 A1 | 7/2010 | Sasaki et al. | |
| 2010/0192686 A1 * | 8/2010 | Kamen | A61M 1/3462 715/764 |
| 2010/0247377 A1 | 9/2010 | Tsutsumida et al. | |
| 2010/0298751 A1 | 11/2010 | Schulte et al. | |
| 2011/0000830 A1 | 1/2011 | Ikeda | |
| 2011/0066043 A1 | 3/2011 | Banet et al. | |
| 2011/0077474 A1 | 3/2011 | Huiku | |
| 2011/0208072 A1 | 8/2011 | Pfeiffer et al. | |
| 2011/0230744 A1 | 9/2011 | Ripoll et al. | |
| 2012/0150049 A1 | 6/2012 | Zielinski et al. | |
| 2012/0181189 A1 | 7/2012 | Merchant | |
| 2012/0203573 A1 | 8/2012 | Mayer et al. | |
| 2012/0228226 A1 | 9/2012 | Castellarnau et al. | |
| 2012/0232364 A1 | 9/2012 | Delmage | |
| 2012/0273415 A1 | 11/2012 | Gerber et al. | |
| 2012/0297869 A1 | 11/2012 | Gagel | |
| 2012/0310135 A1 | 12/2012 | Bauer et al. | |
| 2012/0316465 A1 | 12/2012 | Maier et al. | |
| 2013/0020237 A1 * | 1/2013 | Wilt | A61M 1/301 210/85 |
| 2013/0153474 A1 | 6/2013 | Frorip et al. | |
| 2014/0012097 A1 | 1/2014 | McCrea et al. | |
| 2014/0018727 A1 * | 1/2014 | Burbank | A61M 1/1672 604/28 |
| 2014/0076058 A1 * | 3/2014 | Brugger | G01L 19/0023 73/723 |
| 2014/0148750 A1 | 5/2014 | Pagès et al. | |
| 2014/0199193 A1 * | 7/2014 | Wilt | A61M 1/3609 417/474 |
| 2014/0299544 A1 * | 10/2014 | Wilt | A61M 1/1601 417/474 |
| 2015/0005699 A1 * | 1/2015 | Burbank | A61M 1/282 604/29 |
| 2015/0100009 A1 | 4/2015 | Bearss | |
| 2015/0133854 A1 | 5/2015 | Zhu et al. | |
| 2015/0164370 A1 | 6/2015 | Wabel et al. | |
| 2015/0258277 A1 | 9/2015 | Halpert et al. | |
| 2015/0320363 A1 | 11/2015 | Haan | |
| 2016/0374596 A1 | 12/2016 | Barrett | |
| 2016/0377530 A1 | 12/2016 | Barrett | |
| 2017/0072125 A1 | 3/2017 | Wallenås et al. | |
| 2017/0196517 A1 | 7/2017 | Zhang | |
| 2017/0202493 A1 | 7/2017 | Bezemer | |
| 2017/0224897 A1 | 8/2017 | Kopperschmidt et al. | |
| 2017/0232174 A1 | 8/2017 | Gerlach et al. | |
| 2017/0239409 A1 | 8/2017 | Reyes et al. | |
| 2017/0265793 A1 | 9/2017 | Maierhofer | |
| 2017/0281849 A1 | 10/2017 | Goto et al. | |
| 2017/0296727 A1 | 10/2017 | Burbank et al. | |

(56) References Cited

U.S. PATENT DOCUMENTS

| | | |
|---|---|---|
| 2017/0340801 A1 | 11/2017 | Roger et al. |
| 2017/0348471 A1 | 12/2017 | Goto et al. |
| 2018/0055988 A1 | 3/2018 | Brun |
| 2018/0140761 A1 | 5/2018 | Rovatti et al. |
| 2018/0169315 A1 | 6/2018 | Rovatti et al. |

FOREIGN PATENT DOCUMENTS

| | | | |
|---|---|---|---|
| EP | 2279768 A1 | 2/2011 | |
| EP | 2292283 A1 | 3/2011 | |
| EP | 2388030 B1 | 11/2011 | |
| EP | 2550987 B1 | 1/2013 | |
| EP | 2558967 A1 | 2/2013 | |
| EP | 2656785 A1 | 10/2013 | |
| EP | 2678070 A2 | 1/2014 | |
| EP | 2734111 A2 | 5/2014 | |
| EP | 2735323 B1 | 5/2014 | |
| EP | 2730302 B1 | 12/2014 | |
| EP | 2836112 A1 | 2/2015 | |
| EP | 2670454 B1 | 12/2015 | |
| EP | 2578147 B1 | 4/2016 | |
| EP | 3145393 A1 | 3/2017 | |
| EP | 3231461 A1 | 10/2017 | |
| ES | 54362 U * | 7/1956 | |
| JP | 2008264217 A | 11/2008 | |
| JP | 2009273749 A | 11/2009 | |
| JP | 2009273750 A | 11/2009 | |
| JP | 2009297403 A | 12/2009 | |
| JP | 2009297404 A | 12/2009 | |
| JP | 2009297405 A | 12/2009 | |
| JP | 2010029434 A | 2/2010 | |
| JP | 2011047767 A | 3/2011 | |
| JP | 4905475 B2 | 3/2012 | |
| JP | 5278681 B2 | 9/2013 | |
| JP | 5280874 B2 | 9/2013 | |
| JP | 5301259 B2 | 9/2013 | |
| JP | 5385763 B2 | 1/2014 | |
| JP | 5385764 B2 | 1/2014 | |
| JP | 5548917 B2 | 7/2014 | |
| JP | 2015029882 A | 2/2015 | |
| JP | 2016214367 A | 12/2016 | |
| WO | 2000066197 A1 | 11/2000 | |
| WO | 2007109537 A2 | 9/2007 | |
| WO | 2011130669 A1 | 10/2011 | |
| WO | 2013010677 A2 | 1/2013 | |
| WO | 2013152854 A1 | 10/2013 | |
| WO | 2012116336 A3 | 2/2014 | |
| WO | WO 2014099779 A1 * | 6/2014 | A61M 1/14 |
| WO | 2015179523 A1 | 11/2015 | |
| WO | 2016092913 A1 | 6/2016 | |

OTHER PUBLICATIONS

Extended European Search Report dated Mar. 27, 2020 for European Patent Application No. 17847513.3.
International Search Report and Written Opinion for International Application No. PCT/US2017/049489 dated Dec. 29, 2017.

* cited by examiner

Relationship of Viscosity to Hemocrit level:

Suggests range of 2 – 3 cP for normal HD patient

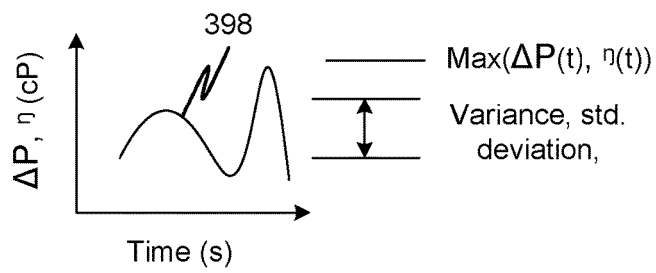
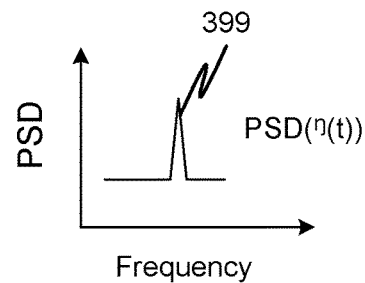
Fig. 7A  Fig. 7B
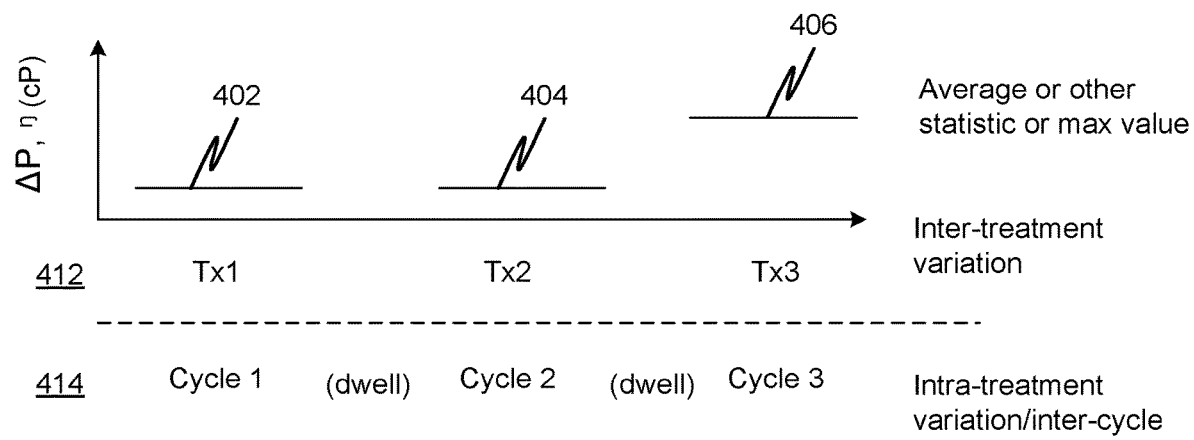
Fig. 8
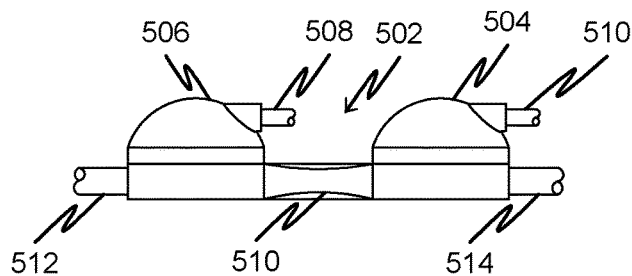
Fig. 10

PARAMETER MONITORING IN MEDICAL TREATMENT SYSTEMS

CROSS-REFERENCE TO RELATED APPLICATIONS

This application is a U.S. national stage filing under 35 U.S.C. § 371 of International Application No. PCT/US2017/049489 filed Aug. 30, 2017, which claims the benefit of U.S. Provisional Application 62/381,413, filed Aug. 30, 2016, all of which are hereby incorporated by reference in their entireties.

BACKGROUND

The present invention relates generally to medical treatments, and more specifically to the control of medical treatments based on the detection of the properties of fluids involved in treatment.

Due to disease or injury, a patient's renal system may lose sufficient function to sustain life. The failure can cause a water imbalance and the accumulation of toxic elements that are no longer properly eliminated. For example, end products of nitrogen metabolism (e.g., urea, creatinine, uric acid, and others) can accumulate in blood and tissues.

There are various forms of renal replacement therapy that can be used to treat renal failure. For example, dialysis removes waste, toxins, and excess water from the body that would otherwise have been removed normally. Dialysis treatment can be life-saving. Hemodialysis, hemofiltration, and peritoneal dialysis are three types of dialysis therapies generally used to replace renal function.

Hemodialysis removes waste, toxins, and water directly from the patient's blood by flowing blood and dialysate through an extracorporeal circuit, and exchanging fluids, solutes, and molecular species across a membrane by diffusion and convection. A patient is connected to a treatment machine and the patient's blood is pumped through a blood circuit. A patient access using needles or catheters may provide access to veins and arteries for the supply and return of blood to and from the treatment machine. The membrane is housed in a dialyzer, a type of filter. As blood passes through the dialyzer, the waste, toxins, and excess water from the patient's blood are removed and the cleansed blood is returned to the patient. During a treatment, as much as 90-120 liters of dialysate may be consumed. Treatments may last several hours and may be performed daily or two to three times per week.

Hemofiltration is similar to hemodialysis but differs in relying more on convection of fluid from the blood and replacement of the fluid with a replacement fluid. Hemofiltration is better at removing larger molecules. To an extent, convection and diffusion play a role in the function of the treatment in both hemodialysis and hemofiltration, and there are treatments that lie in the middle called hemodiafiltration.

Peritoneal dialysis infuses dialysate into the peritoneum, effectively using the peritoneal membrane as the filter to exchange water and dissolved species with the dialysate. The transfer of waste, toxins, and excess water from the bloodstream into the dialysate occurs due to diffusion and osmosis during a dwell period. The spent dialysate is later drained to remove the excess water and other materials.

There are a variety of peritoneal dialysis modalities. Automated peritoneal dialysis includes a drain, fill, and dwell cycle. However, a dialysis machine performs multiple cycles of fill and drain on a schedule that includes a dwell interval. This may be done overnight while the patient sleeps. With automated peritoneal dialysis, the treatment machine connects to an implanted catheter and to a source of fluid and a drain. The machine pumps spent dialysate from the peritoneal cavity, through the catheter, to the drain, and then pumps fresh dialysate through the catheter to the peritoneum. A computer controller may be used to control the machine.

In all renal replacement therapy systems, there is a dire need to maintain sterility to prevent infection. Also, there is a perennial need for improved safety because of the risks associated with repeated treatments and the fact that the patient's blood and peritoneum are so vulnerable to exposure. Still further, there may be further opportunities to extract relevant information about a patient's health and the efficacy of treatments. Still further, there may exist opportunities to use information that is available or which can be extracted readily during treatment in real-time and continuously or discontinuously to aid in the management of equipment, patient health, and treatment efficacy.

SUMMARY

The disclosed subject matter includes devices, methods, and systems for detecting a patient or treatment system status or event, such as a diagnosis of an infection or a patient's fluid status, based on parameters detected using the treatment system. The disclosed embodiments relate to fluid treatment systems or other bodily fluid treatment systems in which a fluid is removed from a patient. Examples include extracorporeal blood treatment systems and peritoneal dialysis systems. According to embodiments, a property of a fluid from a patient is detected and stored as data over a period of time, for example, over a treatment cycle or over multiple treatment cycles. Data from multiple treatments may be stored and used to extract a prediction of temporal profiles expected for future treatments. This predicted profile can be compared to a current profile and used to determine if it indicates a remarkable treatment status or patient status, for example, an infection. Parameters may include temperature and viscosity of the fluid or any other parameter indicative of a physical or chemical property of the fluid. In embodiments, the parameter may be proportional to viscosity. These may be absolute parameters or relative parameters—an outgoing fluid parameter taken relative to an ingoing fluid parameter. Trends in these parameters may be combined with other parameters measured otherwise to allow them to be correlated for specific patients. For example, fluid volume status may be correlated with viscosity and hematocrit to create a custom model that can predict one of these given one or more of the others. In addition, dynamic trends in these parameters and others may be combined over a treatment or over one or more days/treatments, the parameters including, for example, pH, hematocrit or hemoglobin level, heart rate, blood pressure, blood oxygenation, as well as other parameters either directly measured or stored in a data log. Conditions may be automatically changed and time trends recorded to yield additional diagnostic data. For example, a temporary reduction or halting of ultrafiltration during a treatment with time-based sampling of blood viscosity can indicate the rate of movement of fluid from the interstitial compartment to the blood compartment, and/or indicate whether further ultrafiltration is needed.

It will be observed that the methods, devices, and systems disclosed may be employed in various combinations to, among other things:

a. improve the diagnosis of a patient undergoing a treatment, and in particular, a renal replacement therapy or extracorporeal blood treatment;
b. using single or multiple real-time sensor signals alone or in combination with logged data, detect correct or incorrect operation of medical treatment equipment or operator error that could lead to incorrect operation of medical treatment equipment;
c. improve renal replacement therapy or extracorporeal blood treatment outcomes; and
d. detect patient water content and/or ultrafiltration rate during a blood treatment continuously or discontinuously and in real-time.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 7A is a figurative illustration of the time-variation of a parameter related to (preferably proportional) to viscosity which may occur over a course of a drain cycle of a peritoneal dialysis treatment for purposes of discussing statistics that may be used to identify a potential infection, according to embodiments of the disclosed subject matter.

FIG. 7B is a figurative frequency domain signal derived from the time variation of a parameter related to (preferably proportional) to viscosity which may be based on a window function spanning seconds to minutes occur over a course of a drain cycle of a peritoneal dialysis treatment for purposes of discussing features that may be used to identify a potential infection, according to embodiments of the disclosed subject matter.

FIG. 8 shows a metric of a parameter related to viscosity over multiple treatments or multiple cycles with each bar 402, 404, 406 showing a given treatment or a different drain cycle of peritoneal dialysis all develop over time in order to illustrate that remarkable changes in the parameter in a given cycle or a given treatment may be used to identify a possible condition such as an infection of the peritoneum.

FIG. 10 shows a "double pod" article of manufacture that may be used in place of a single pressure sensor in a fluid circuit such as a blood circuit for pressure detection and viscosity-dependent pressure loss measurement.

DETAILED DESCRIPTION

Figure 1:
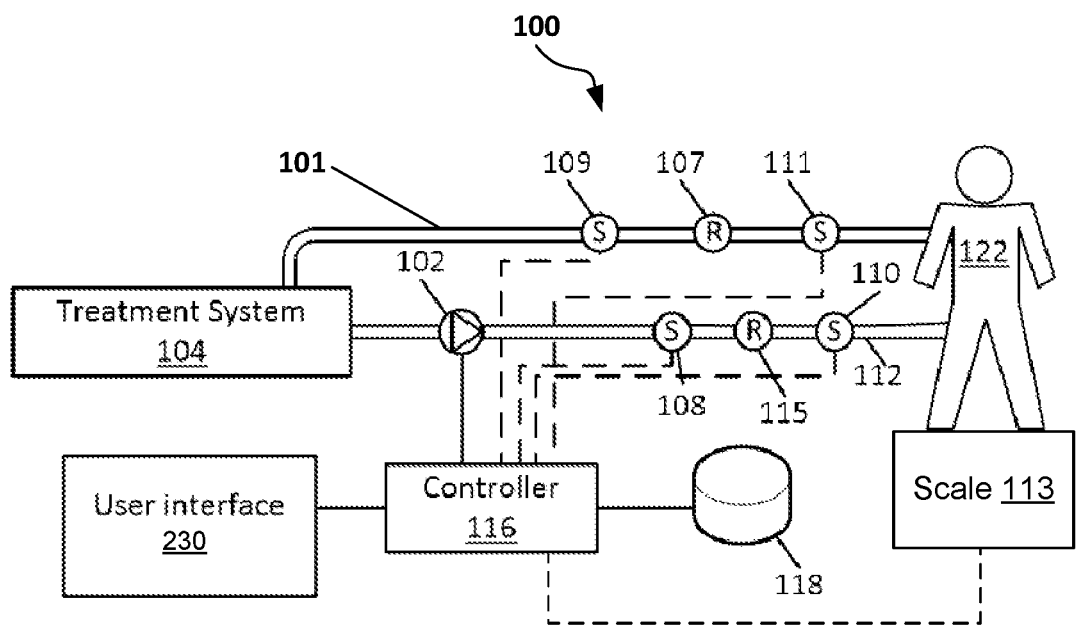
FIG. 1 is a schematic illustration of a peritoneal dialysis or hemodialysis system, according to embodiments of the disclosed subject matter.

A generalized system 100 is shown in FIG. 1. A treatment system 104, which may include a blood treatment device that transfers a fluid, such as blood, from and to a patient 122. The system may also represent a peritoneal dialysis machine that transfers peritoneal dialysate to the patient 122 and withdraws peritoneal dialysate from the patient 122. Fluid is conveyed via a fluid circuit 101 that includes lines 112 that engage, or expose contents to, one or more sensors 109, 111, 108, 110. Sensor signals of sensors 109, 111, 108, 110 are conveyed to a controller 116 which may control pumps such as pump 102, and other pumps not shown, as required. Sensor signals of sensors 109, 111, 108, 110 may also be used by controller 116 to display and/or record patient status/data, transmit patient status/data to a healthcare provider or any other person, device, or entity (e.g., via paging, email, text messaging, treatment log, network server), control delivery of a medicine to the patient (e.g., by controlling an IV or a substance added to the fluid in lines 112).

Fluid may be conveyed through flow restrictions 107, 115 to facilitate measurement of a parameter of the fluid, for example, a viscosity of a respective one of blood or peritoneal dialysate in various embodiments. However, any other known means of measuring viscosity may be used in alternative embodiments, such as any known viscometer or rheometer or by using an optical technique. Captured measurements may be stored by the controller 116 on a non-volatile data store 118 that resides locally or in the cloud.

With regard to any of the embodiments disclosed herein, including the claims, pressure loss through the flow restriction may be used to detect a fluid's viscosity. The calculation may involve the use of an empirical conversion constant for the flow restriction 107, 115 obtained from experiments with the particular fluid and low regime (i.e., turbulent vs laminar) of interest. Some fluids, such as blood, have a viscosity that varies with the shear rate so comparable viscosities may be measured at predefined flow rates or within predefined ranges of flow rates. The pressure loss for a predefined configuration, flow rate, and fluid properties (e.g. density, for turbulent flow) other than viscosity may be identical, or made to be identical by the controller (e.g., flow rate) from one measurement to the next. The controller may control a pump or pumps to establish a predefined flow rate stored in a memory by the controller for purposes of performing a viscosity measurement. The flow rate may be temporarily established for the purpose of measurement and controlled to other flow rates at other times. Preferably viscosity is measured at Reynolds numbers in the laminar regime (<2100 or <2300) which makes the pressure loss invariant with respect to density. Since blood density is proportional to total protein, the water loading of the blood compartment of the patient will be density sensitive. Thus the laminar flow regime simplifies the measurement of viscosity. As pointed out elsewhere, since for a predefined flow system (restriction 107, 115 including the pressure sensors, the restriction for example being a straight length of tubing or a curved tube having a predefined diameter, an orifice, a smooth contraction, or other type of restriction) and a predefined flow rate, the pressure difference indicated by the pressure sensors is simply proportional to viscosity for laminar flow, thresholds for response can be established in terms of pressure drop. In other words it is not necessary to convert pressure drop to viscosity because the latter differs from pressure drop only by a constant of proportionality. To extend the embodiments to turbulent flow (Re>2000) the pressure loss depends on density. The above features are well-known from empirical equations for calculating pressure drop in fluid flow fixtures, for example, Darcy Weisbach equation and Hagen-Poiseuille equation.

The controller 116 may or may not have control functions such as operating the pump 102 or pumps and may be embodied in a stand-alone processor. Alternatively, controller 116 may control the treatment system 104 and/or the pump 102, in order to take an action responsively to a detected status or to enhance the acquisition of data relating to the patient or treatment being administered.

In embodiments, the one or more sensors 109, 111, 108, 110 may include one or more pressure sensors or pressure pods, blood oxygen level sensors, pulse sensors (which may be combined as pulse-oximeter), temperature sensors, pH sensors, or other sensor types that measure a physical, chemical, or other parameter of a fluid. System 104 may alternatively or additionally include a weight scale 113 that provides a signal indicative of the weight of the patient 122, and the controller 116 may use such signal, instead of or in combination with signals produced by the one or more sensors 109, 111, 108, 110, to implement any functionality described herein with reference to a treatment of the patient 122. As indicated elsewhere, the flow restriction 107, 115 may include tubing or all or part of the pressure sensors 109, 111, 108, 110.

In some alternative or additional embodiments, system 100 may transfer a fluid other than blood or peritoneal dialysate from and to the patient 122, such as urine, lymph, cerebrospinal fluid, amniotic fluid, synovial fluid, etc. In these embodiments, sensors 109, 111, 108, 110 may measure any physical, chemical, or other property of the fluid, and thus may be used by controller 116, alone or in combination with other sensor data from any other sensors, to display and/or record patient status/data, transmit patient status/data to a healthcare provider or any other entity (e.g., via paging, email, text messaging, etc.), control delivery of a medicine to the patient (e.g., by controlling an IV or a substance added to the fluid in lines 112), etc. Again, the fluid may be conveyed through flow restrictions 107, 115 to facilitate measurement of viscosity. However, any other known means of measuring viscosity may be used in alternative embodiments.

As indicated, certain embodiments relate to peritoneal dialysis treatments. As discussed in United States Patent Application US20140018727 (incorporated by reference in its entirety herein), a peritoneal fill/drain line may include a distal fluid pressure sensor located near the patient connection and a fluid pressure sensor near the inlet to a peritoneal dialysis (PD) cycler. The fluid path between the two sensors creates a restriction such that when fluid is pumped to or from the patient, a pressure differential is produced that indicates the fluid viscosity. The viscosity can indicate various processes that may require intervention, including disease, fluid level, or other factors that may affect treatment or patient health.

Embodiments provide improvements on this art. In embodiments, by measuring pressure drop across elements of a fluid circuit that are already in place for treatment, the cost of consumables is minimized. For example pressure sensors may be present for other purpose such as detection of arterial or venous pressure, out-of-bounds operating conditions, for pump inlet pressure compensation for accurate flow conversion from pump speed to flow rate base on pump curves, or other purposes, if separated by a flow path that can function as a flow restriction (all flow paths can but preferably such a flow path provides laminar flow) and the only additional components needed are those that are required for detecting pressure. Such pressure sensors may thus already define a structure such as discussed above with respect to pressure sensor 109 and pressure sensor 111 linked by a flow restriction 107 (similarly for pressure sensor 108 and 110 linked by flow restriction 115). In other embodiments, the existence of a pressure sensor and a flow path that provides resistance may be supplemented by a single additional pressure sensor to provide the components needed for measurement of viscosity. In either case, a controllable pump may also be in place in the treatment system for performing treatment.

Thus, in embodiments, the pressure sensor or sensors may be pressure sensors that perform functions other than viscosity measurement. The line through which pressure drop is measured may include a blood line. The viscosity may be used alone or in combination with other data to generate parameters for detecting a condition of the treatment or the patient. In embodiments, using pressure pods allows a separation of the transducer, which can be permanent and connected to the treatment machine, and allows the placement of the pod anywhere on the circuit.

Examples of other purposes for which the pressure sensors of the embodiments may be used include (1) testing line or connection integrity by pressure-decay testing, (2) peristaltic pump flow control based on inlet pressure compensation, (3) pressure monitoring for out-of-bound conditions, (4) blood or peritoneal cavity pressure measurement. In such cases, the pressure sensors may also provide for viscosity detection and for other functions as described herein.

Using A Flow Restriction

The pressure sensor arrangement of FIGS. 2A, 3A, 3B, 4A, 4B, 6A through 6K of US20140018727 and other embodiments provide proximal and distal pressure sensors which are used to measure pressure drop along the PD fill/drain line. Such arrangement of the PD fill/drain line, including the amount and degree of curvature of the flow path, whether it is pinched in places or not, can vary from treatment to treatment.

In some embodiments, to avoid problems with using the fill/drain line (or separate fill and drain lines, if present), a flow restriction that is resistant to variation from one treatment session or tubing set to another may be provided. Pressure detection through this repeatable flow restriction is used to obtain pressure drop data that may be used to detect viscosity or variations thereof (e.g., hemoglobin or hematocrit) as described herein. A rigid tube length with low manufacturing tolerance (lower than other portions of the fluid circuit) may be provided. In embodiments, a single housing with two pressure pods joined by a rigid injection-molded port or tube length may be provided, the latter defining a flow restriction (e.g., 107, 115). Such a "double pod" may be used in any fluid circuit having a portion where a pressure measurement is required (e.g., pump inlet pressure compensation, venous pressure, or arterial pressure). FIG. 10 shows a "double pod" 502 article of manufacture that may be used in place of a single pressure sensor in a fluid circuit such as a blood circuit for pressure detection and viscosity-dependent pressure loss measurement. A first pressure pod 506 is joined to a second pressure pod 504 by a flow path element 510 which defines a restriction as discussed elsewhere in the present disclosure. These elements may be formed of a single housing. Air sensor lines 508 and 510 connected to pressure transducers. Fluid, such as blood, flows through ports connected to inlet and outlet lines 512 and 514.

In embodiments, examples of flow restrictors which may be added to those of FIGS. 2A, 3A, 3B, 4A, 4B, 6A through 6K of US20140018727, hereby incorporated by reference as if fully set forth herein, or as alternatives thereto, include an orifice and a rigid channel. Pressure sensors may be arranged on either end of the flow restriction. One or both of the pressure sensors that measure the pressure drop may include any pressure sensor known in the art such as any of those shown in the FIGS. 2A, 3A, 3B, 4A, 4B, 6A through 6K of US20140018727. In embodiments, the flow area of the fill/drain line between the flow restriction and the pressure sensor may be large enough such that the flow restriction presents a much greater restriction to flow than the rest of the fill/drain line. With such a configuration, variability in the arrangement of the PD fill/drain line, inner diameter, the amount and degree of curvature of the flow path, whether it is pinched in places or not, for example, may introduce a minor and tolerable variation in the viscosity calculated from the pressure drop. In embodiments, the flow restriction may be sized to create a pressure drop that is a predefined number of times greater that the greatest typical variation created by variations in the above parameters.

Indicating A Trend in Viscosity

In embodiments, as an additional feature that may be provided to improve a function to detect conditions indicated by viscosity changes and magnitudes, the system may capture and analyze historical trends of viscosity (and optionally combine historical trends with other data as discussed later). In embodiments, the pressure drop data is recorded during a treatment, including, optionally at least, at multiple times during a single treatment to create a record over time of the pressure drop data. These pressure data may be used with predefined configuration data stored as a model or with empirically-derived data to generate a trend or instance of viscosity over time during a treatment. As indicated, the pressure drop can be used without conversion, in embodiments. The trend or instant (or statistic derived from a trend) may be stored in a patient profile and referred to during each treatment for comparison by a microprocessor. In embodiments, when a viscosity associated with a current treatment is different according to a predefined characteristic from a predefined prediction of viscosity based on historical pattern, an indication of the departure may be generated and output to a user interface, a physician, a technician, a treatment log, a nurse, a nurse station, or any other receiving person or device. Further, such data may generate a response in the PD system such as a warning or shutdown.

Still another alternative or additional embodiment monitors the pressure drop caused by flowing blood in an extracorporeal blood treatment system such as a hemodialysis system. Using a similar system attached to measure pressure loss in a blood line or flow restrictor, the change in the blood viscosity can be monitored, predictions based on historical trends generated, and so on as discussed above. Since blood is non-Newtonian (shear-thinning), a viscosity description may be generated and stored for comparison to measured conditions during a treatment. For example, an empirical prediction model such as: a normalized stress/strain profile or, assuming a controlled flow geometry, pressure loss/mass flow profile, may be generated from historical pressure data for comparison to instant conditions during a treatment. The prediction of pressure drops (or shear) may be further refined based on hematocrit measured using a sensor or stored data. In alternatives, viscosity, or pressure-drop alone, may be detected and compared to thresholds for predefined flow geometry (between the pressure sensors) and conditions such as flow rate and blood temperature. In other embodiments, the viscosity may be measured at multiple flow rates and compared as independent parameters or the viscosity at the multiple flow rates may be averaged. Instead of viscosity, the pressure drop divided by flow rate may be used for laminar flow.

In embodiments, blood viscosity data are collected in combination with blood flow rate data to indicate the instant blood flow rate at each viscosity measurement. Alternatively, viscosity (or pressure drop) is measured at a pre-defined flow rate. In embodiments, blood viscosity measurements are performed at controlled blood flow rate levels. For example, embodiments first reduces/increases the blood flow rate in lines 112 to reach a pre-defined level and then measures blood viscosity at the pre-defined blood flow rate level. Embodiments repeats blood viscosity measurements to obtain a reliable measurement, for example, by discarding outlier measurements, by averaging all or a subset of the measurements.

During PD therapy, there is a drain phase in which used dialysate (effluent) from the patient is pumped to drain. This phase typically includes a period during which fluid is removed from the patient at a fixed rate (typically between 200 and 400 mL/min). For a fixed pumping rate, the pressure drop between the distal pressure sensor and the pump inlet sensor is proportional to the viscosity. The cycler can measure the pressure at these two sensors (at a suitably high sampling rate) and calculate an average pressure drop, which can be converted to a value that is proportional to the effluent's viscosity.

By recording the average pressure drop during certain portions of each drain cycle, a profile can be generated for a given patient that reflects his or her typical effluent viscosity for each drain cycle. Over a period of time, this data can be used to statistically characterize that patient's "viscosity as a function of drain cycle" profile.

The values computed for a given day's treatment can be communicated to a relevant health care professional (HCP) as part of a daily treatment record, along with a comparison to the patient's average "viscosity vs. drain cycle" profile or prediction.

If, on a given day or at a given time, there is a significant deviation (indicated by a change beyond a predefined range stored in the controller) in the patient's viscosity, that fact can be highlighted by the controller in the output to the patient's daily treatment record, signaling to the HCP that there has been a significant change indicated by a detected difference from a predefined threshold. Significant changes in effluent viscosity can be triggered by the onset of infection, hence this can provide HCP's with an early indication of infection, allowing for rapid intervention/mitigation. In embodiments, a significant change is a change that is beyond a predefined magnitude. In embodiments, the predefined magnitude is determined based upon a statistics derived from viscosity or other measurements in a group of patients or from historical viscosity or other measurements of a single patient.

During hemodialysis (HD) therapy, a similar approach can be used during the course of a treatment to monitor changes in the viscosity of a patient's blood during the course of treatment. Generally, blood viscosity varies with hematocrit levels. When pumping blood, any pair of inline pressure sensors may detect pressure differentials across a flow restriction such as an orifice or length of tubing, while pumping; these pressure differentials will be proportional to the blood's viscosity, and hence, to the hematocrit concentration. Normal values for Hematocrit are known in the art, for example, as follows:

Renal patients may have abnormal, usually low, hematocrit. This is often treated with medication. Even normal patients vary, but in general there is a trend as follows:
Male: 40.7 to 50.3%
Female: 36.1 to 44.3

Normal results for children vary, but in general are as follows.
Newborn: 45 to 61%
Infant: 32 to 42%

Figure 2:
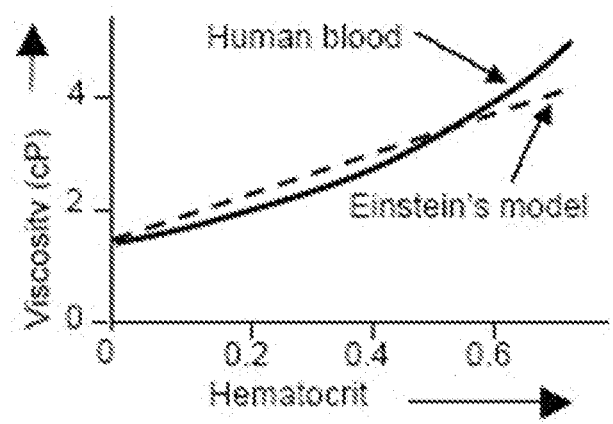
FIG. 2 is a graph showing the relationship between viscosity and hematocrit level.

FIG. 2 shows an example graph of a relationship between viscosity and hematocrit compared to the Einstein theoretical model for a dilute suspension. It shows that the viscosity is more sensitive to the concentration of blood cells than would be predicted by the model. Patient treatment logs or other output such as on a user interface may include the output of hematocrit or hemoglobin based on a conversion from the viscosity or pressure drop data. The hematocrit or hemoglobin may be compared to predefined ranges stored by the controller to indicate abnormal conditions which may be highlighted in the output data or cause the controller to generate a corresponding indication.

Indicating Whether Dry Weight Has Been Reached

In embodiments, by monitoring changes in blood viscosity (and hence, hematocrit concentration) during the course of an HD treatment, a treatment system or connected digital monitoring system determines when a patient has reached their dry weight, and adjust the therapy such that the rate at which ultrafiltration occurs is appropriately related to the rate at which the patient's body is able to replace blood fluid volume. Dry weight indicates a normal level of water in the patient. It may be characterized by reference to the patient's weight when the normal fluid levels are achieved or by the normal concentration of blood constituents. Ideally, a patient should leave a dialysis treatment at his or her dry weight. An increase in viscosity above this "plateau" can provide an early indication that the patient might be about to experience a hypotensive episode or "crash" due to low blood fluid volume.

When using viscosity measurement of the blood during an extracorporeal treatment that also includes fluid removal from the patient (i.e., ultrafiltration or UF), besides continuously monitoring the rate of change in hematocrit for values that exceed predefined limits as described above, the UF can be reduced or completely halted for a brief period of time to allow the cellular/interstitial fluid volume to equilibrate with the blood. If the patient's measured pressure drop, hematocrit, and/or viscosity does not change (or shows a change smaller than a predefined range) during the reduced/halted UF period, the patient may be determined by the controller to be at the patient's dry weight. More specifically, the controller 116 may store multiple samples of pressure drop information (or the pressure data reduced to viscosity or hematocrit according to a stored formula or lookup table) to determine a trend in viscosity and/or hematocrit during the reduced/halted UF period. If the patient's measured indicator falls during the reduced/halted UF period, the patient may be determined to have not reached their dry weight, and therefore more fluid can be removed. The amount of this "rebound" of viscosity/hematocrit can be used by an automated controller to cause a change in the UF rate including halting UF altogether. If the viscosity/hematocrit does not change during the reduced/halted UF period, the controller 116 may generate an indicator that the patient may have reached their dry weight and it may cease further ultrafiltration as well as indicate the detected condition via the user interface 230. This effect, called rebound, is detected indirectly using pressure drop, viscosity, and/or hematocrit. The magnitude of this rebound in hematocrit indicated by viscosity can also be used by the controller 116 to alter the rate of UF as well. For example, the UF rate may be controlled by the controller 116 such that the rate is constant and such that the patient reaches their dry weight at the end of a scheduled termination of treatment or at a predefined time before a scheduled end of treatment.

Figure 3:
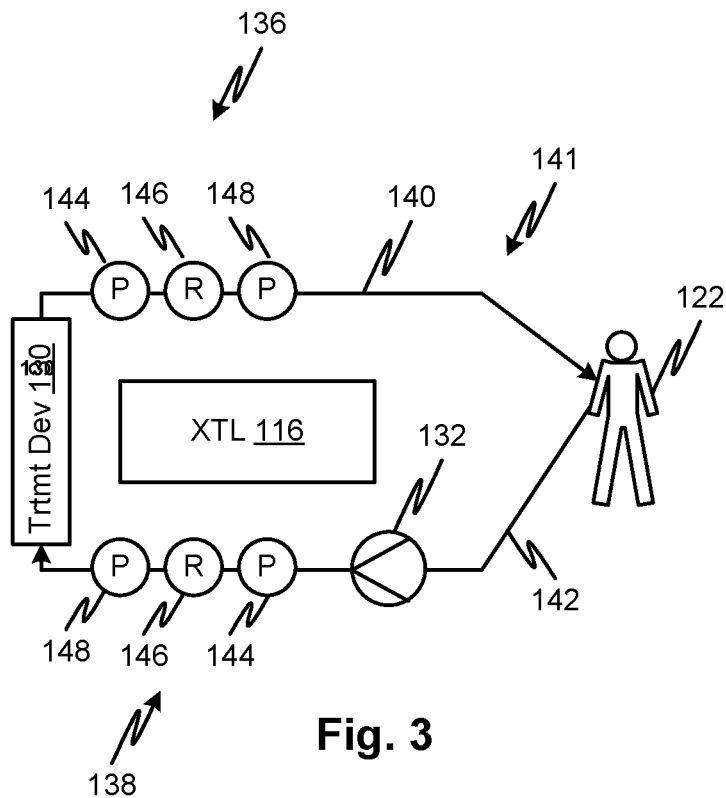
FIG. 3 shows a schematic illustration of a feature of a hemodialysis system, according to embodiments of the disclosed subject matter.

Referring to FIG. 3, a blood circuit 141 has a venous line 140 and an arterial line 142 connectable to a patient 122. A pump 132 pumps blood through the arterial line 142, through a treatment device 130, through the venous line 140 back to the patient 122. The arterial line 142 has a viscosity detector 138 that includes an upstream pressure sensor 144 and a downstream pressure sensor 148 with a flow restriction 146 between them. Similarly, the venous line 140 has a viscosity detector 146 that includes an upstream pressure sensor 144 and a downstream pressure sensor 148 with a flow restriction 146 between them. The flow restrictors 146 may be a tube with a predefined shape and inner diameter, a precisely sized port with a shaped inlet and outlet or any other suitable device for generating a viscosity—indicating pressure change when fluid flows through it.

The configuration of FIG. 3 provides an arrangement in which the viscosity of blood may be determined at the entry of the treatment device 130 and at the exit of the treatment device 130 so that the viscosity and/or derived hematocrit properties in and out of the treatment device may be compared by the controller 116. The viscosity may be used by the controller as an indicator of a change in hematocrit by converting the viscosity to a hematocrit using a function such as represented by FIG. 2. The hematocrit level can be converted to an estimate of the water content of the blood. The water content levels entering and leaving the treatment device 130 can provide an independent estimate of an instantaneous ultrafiltration rate. The latter may be numerically cumulated over time to estimate the total fluid gained or lost during a treatment.

Estimating Ultrafiltration Rate

Many extracorporeal blood treatments, such as renal replacement therapy, remove water as part of their treatment function. In embodiments, by calculating the instantaneous ultrafiltration rate, the controller 116 may be enabled to control the rate, for example to limit it to a predefined rate and no higher or to limit the cumulated fluid gained or lost according to a prescription. As for the rate of fluid removal or ultrafiltration rate, it may be advantageous to limit this parameter for a number of reasons, including to limit the risk of forming clots in the fluid circuit including the treatment device and/or to limit the imbalance between the patient water level in the blood and interstitial compartments. To draw water at a desired rate and also provide a precise control of the total volume withdrawn during a treatment, extracorporeal blood treatment machines are required to maintain precise control of the difference between the volume of arterial blood drawn from a patient and the volume of venous blood returned to the patient. Balancing mechanisms are known in the art for this purpose, but none are perfect. Balancing mechanisms may generate an independent estimate of ultrafiltration rate based on a pump speed, fluid weight, flow rate, or other mechanism, depending on the type of balancing mechanism and according to known principles.

However, in embodiments, such estimations may be combined with ultrafiltration rate estimated as described herein (e.g., based on direct hematocrit measurement or based indirect hematocrit measurement as a function of viscosity—or other) to detect a treatment error or to verify or improve estimates, for example by averaging the two estimations and controlling ultrafiltration responsively to the average. The ability to monitor hematocrit continuously provides an additional way of control and insurance against flawed functioning of the fluid balance system of the extracorporeal treatment system.

In embodiments, the controller 116 may compare the hematocrits of blood entering and leaving the blood treatment device 130 and compare to an estimate of the fluid balancing component used to determine the ultrafiltration rate. If the estimates of these two subsystems vary by a predetermined amount, the controller 116 may output an indicator of the variance. This indicator may be used by the controller to shut down an ongoing treatment automatically and/or create a signal to an operator.

Figure 4:
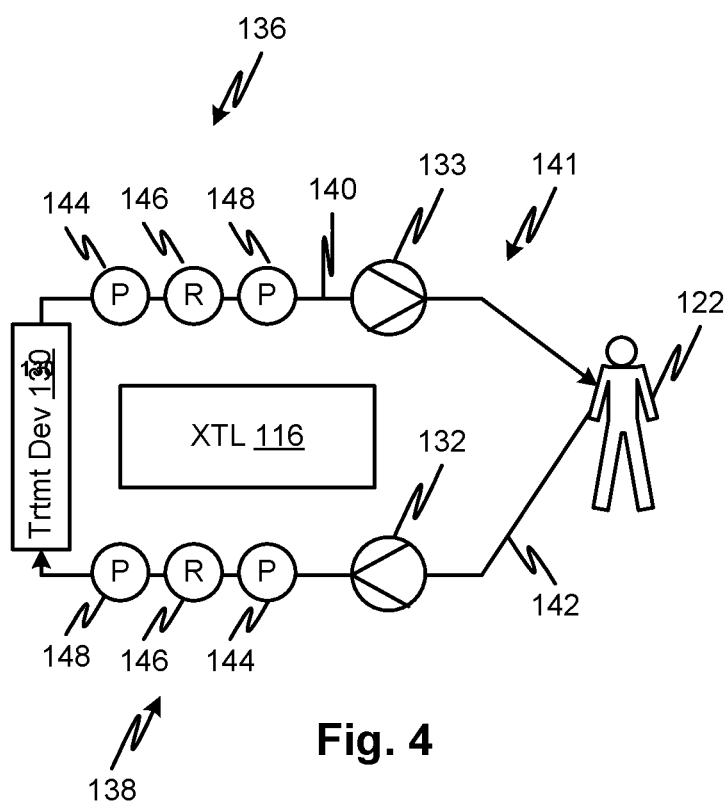
FIG. 4 shows a schematic illustration of a feature of a further hemodialysis system, according to embodiments of the disclosed subject matter.

FIG. 4 illustrates an embodiment which is the same as FIG. 3 except that the system 136 includes two blood pumps, a venous blood pump 133 and an arterial blood pump 132. The volume per unit time pumped by each pump determines the net rate of fluid removal from the patient 122. It will be evident to the skilled person that a variety of mechanisms are available in the art for controlling, under control of the controller 116, the net rate of fluid removal and that the example shown is only one of these. The system of FIG. 4 may be used to allow the controller to select a current rate of UF at any point during a treatment and to vary it according to a selected control scheme. This function may be used to provide a reduction or pause in UF during treatment to allow the measurement and recording of a trend in viscosity over time or a trend in hematocrit by deriving and recording the same from multiple viscosity measurements over time. The rebound of hematocrit after a period of UF is known to be an indicator of whether it is safe to remove additional fluid from a patient.

The present system allows this determination to be made automatically during a treatment and at multiple times by building into the operational profile a series of positive UF intervals with UF reductions/pauses between them. The controller 116 may generate an indicator of a rebound magnitude and rate, for example a graph, and use that to make an automatic determination of whether to halt or reduce the rate of UF or to increase it. The indicator may also be displayed on a user interface.

Note that although embodiments described detect viscosity by using a flow restrictor and pressure sensors, through which all of the blood being treated flows, there are other mechanisms for continuously sampling viscosity. For example, microfluidic samples can be removed from a flow stream at intervals and applied to a viscometer that detects viscosity and generates a signal thereby. Destructive testing can be used where they rely on very small sample sizes. A sampling event may be triggered by a command to test the blood viscosity or the event may be triggered automatically by the controller 116. There are a variety of technologies suitable for measuring blood viscosity, and pressure drop across a restriction (such as a capillary) is only one.

As mentioned above, the pressure sensors used to detect viscosity (and changes thereto) can be arranged in various ways. In embodiments, for example, two sensors may be placed in series in the arterial bloodline, post blood pump, pre-dialyzer, in examples, separated by a molded tube which may act as a flow restrictor with appropriate properties for the purpose. Another embodiment may use a patient arterial blood line as a flow restrictor in a manner that is similar to the use of the fill/drain line described for PD.

Using Data Profiles And Classifiers

For PD treatments, the use of data to create an average "viscosity versus drain cycle" profile for a given patient, and comparing a given day's data to that average to flag significant deviations, may provide an early indicator of infection (peritonitis) or other complications related to PD therapy such as bleeding.

In HD treatments, data may be developed during treatment to establish a baseline viscosity/hematocrit level. Later, this baseline data may be compared to subsequent treatments to detect changes. Viscosity/hematocrit may be monitored throughout a treatment, and a trend therein over the course of a current treatment may be compared to trends, or an average trend (baseline average trend or baseline trends), during previous treatments of the same patient, multiple patients, or a corresponding class of patients.

A baseline temporal profile of viscosity/hematocrit can take the form of a viscosity/hematocrit level and/or an error range, both of which may be developed using statistics cumulated over multiple treatments over a period of time. In addition to, or as an alternative to, a temporal curve of mean or error band, other statistics may be generated. For example, a worst-case rate of change of viscosity may be developed using a patient's previous history, and data responsive to the worst-case change (over time and during a single treatment) in viscosity can be compared to a current temporal profile of viscosity versus time. Other features of a curve can also be extracted and generalized, including the parameters of fits to functions (e.g., orthogonal series, power series, least squares fit to other functions such a Gaussians) may be used to represent both a current evolving time series of viscosity/hematocrit measurements and a baseline.

The baseline parameters may be derived from the treatment of a particular patient so that each establishes a custom individual baseline. Alternatively, patients can be classified and a baseline can be shared among the patients in a respective class. The temporal profile of viscosity/hematocrit over time may define a multi-dimensional feature space that can be applied to a classifier to diagnose various conditions including a pinched line, hypovolemia, low HCT, high HCT, a disease, a correct or incorrect dialysate composition, and other conditions. Generally, a classification is a problem in machine learning and statistics that aims to classify an observation as a member of a number of known classes. A classifier may be trained given a set of known classes and a set of observations with known class memberships. In embodiments, the feature space may be augmented with other inputs such as patient weight, measured HCT, cardiac rate, blood oxygen level, respiration rate, galvanic skin resistance, core temperature, skin temperature, peripheral temperature, measured patient activity level, and/or other parameters. Measured patient activity level may be detected by accelerometers or force sensors in the patient's bed or chair, a video stream classifier receiving input from a live view of the patient's body, detected Internet activity attributed to a patient's Internet-connected terminal, detected telephone usage, a classifier receiving input from a live audio stream from a microphone in the vicinity of the patient, and/or other parameters.

In the above embodiments, a viscosity of a fluid from a patient is monitored directly or indirectly over a period of time during a treatment. All of the above embodiments may be modified to monitor and use temperature of the fluid in the same way. According to such embodiments, temporal temperature profiles may be stored as curves for each patient and compared to a current trend of temperature during a treatment. Other conditions of the treatment such as the temperature of the fluid going to the patient may also be combined with the temperature of fluid being withdrawn from the patient and/or with the fluid mass flow rate to generate a heat loss or gain output to the fluid. These temperature-based parameters may be used in the same way as discussed with respect to viscosity to classify a condition of the treatment or a condition of the patient. For example, a patient with a fever may output more heat than a patient that is afebrile.

In the above embodiments, a viscosity or temperature of a fluid from a patient is monitored over a period of time during a treatment. All of the above embodiments may be modified to monitor and use temperature of the fluid, in the same way, in combination with the viscosity. According to such embodiments, temporal temperature profiles and viscosity profiles may be stored as curves for each patient and compared to a current trend of temperature and/or viscosity during a treatment. Other conditions of the treatment such as the temperature and viscosity of the fluid going to the patient may also be combined with the temperature and viscosity of fluid being withdrawn from the patient and/or with the fluid mass flow rate to generate a change in the respective parameter including heat loss or gain output to the fluid. These combined parameters may be used in the same way as discussed with respect to viscosity to classify a condition of the treatment or a condition of the patient. For example, a patient with a fever may output more heat than a patient that is afebrile. By combining a classification signal indicating a fever with a classification signal indicating a change in viscosity, both generated relative to a baseline expectation, the classification estimate's reliability can be increased. For example, if both temperature and viscosity tend to indicate an infection, the classification by the controller of the existence of an infection is more reliable.

In any of the embodiments above, the viscosity and/or temperature flow to the patient, as well as returning from the patient, may be monitored to determine a change in the respective property which may be stored in addition to the respective property or instead of the respective property. The stored baseline data representing predicted parameters may be attended by, or replaced by, stored baseline data for prediction of the respective change from patient-ingoing to patient-outgoing fluid parameters.

The mapping of measured changes in viscosity, along with other parameters, to conditions, may be generated using various methods including artificial intelligence techniques. Examples include supervised and unsupervised learning techniques to generate classifiers including naive Bayesian classifiers, self-organizing maps, and neural networks.

Example Implementation

One example embodiment implements a fill/drain line for PD or a blood line for extracorporeal blood treatment. The example embodiment includes a 12 ft. PD fill/drain line created from tubing—Teknor Apex MD-50263 thermoplastic elastomer, 4.0 mm×7.0 mm ID/OD. In the example embodiment, non-contacting pressure sensors are installed at the beginning and end of this line to measure pressure drop and calculate viscosity from the pressure drop and flow rate based on empirical or theoretical data. In respective embodiments, the pressure sensors may be located on either side of a flow restrictor, which may be a length of the fill/drain line or some flow restriction element in the fill/drain line.

In any of the foregoing embodiments, a treatment system may be controlled to modify the rate of flow of fluid, or to halt the flow of fluid for an interval, in order to increase an effect such as heat transfer to the fluid or the recruitment of viscosity changing elements into the fluid from the patient's body. This may increase the property signal and make machine classification diagnosis more reliable. In embodiments, the controller may first make a classification based on unmodified flow rates or flow regimens (e.g., in the absence of any halting of the flow), and then in response to a weak diagnostic reliability estimate of the classification, modify the rate of flow of fluid or halt the flow of fluid for an interval, thereby enhancing the parameter change that is monitored.

In any of the foregoing embodiments, hematocrit can be measured directly using an optical sensor. Optical sensor technologies capable of measuring the volume concentration of red blood cells are known. For example, they may employ optical coherence tomography and may detect absolute magnitudes in a fluid line carrying blood or changes in the body by means of a low-penetration sensor applied to the skin. Such independent indications of hematocrit level may be combined with those described above calculated from viscosity or used as an alternative thereto. The hematocrit may thus be measured at the inlet and outlet of the treatment device and an ultrafiltration rate may be calculated from these. More traditional hematocrit measurement methods may be employed as well, for example, automatically extracting a small sample for centrifugation and measurement of a packed cell volume therefrom.

In any of the foregoing embodiments, the personal profile data of a patient may be stored as a fit to predictive model of a patient—treatment device system. In such embodiments, the predictive model may be adapted to account for the impact of the flow rate or ultrafiltration rate modification. The predictive model may permit the estimation of an ideal ultrafiltration and flow rate or any other treatment parameter. The predictive model may receive, as parameters, additional data relating to the patient, such as weight, body mass index, sensitivity to pyrogens, body fat, circulatory health, peritoneum health or indicia such as PD treatment history, etc. These additional data may be parameters of the model of the patient that are used to customize the model for the patient, thereby improving the accuracy of classification based on the model.

Fluid Sampling

Figure 5:
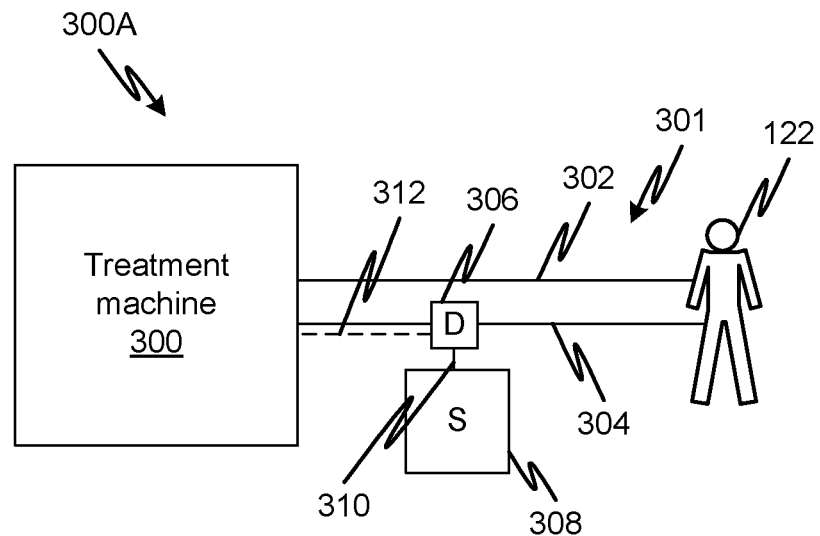
FIGS. 5 and 6 show embodiments of systems that automatically divert a sample of fluid responsively to an estimation signal indicating the presence of, or a probability of, a condition of interest such as a patient infection.
Figure 6:
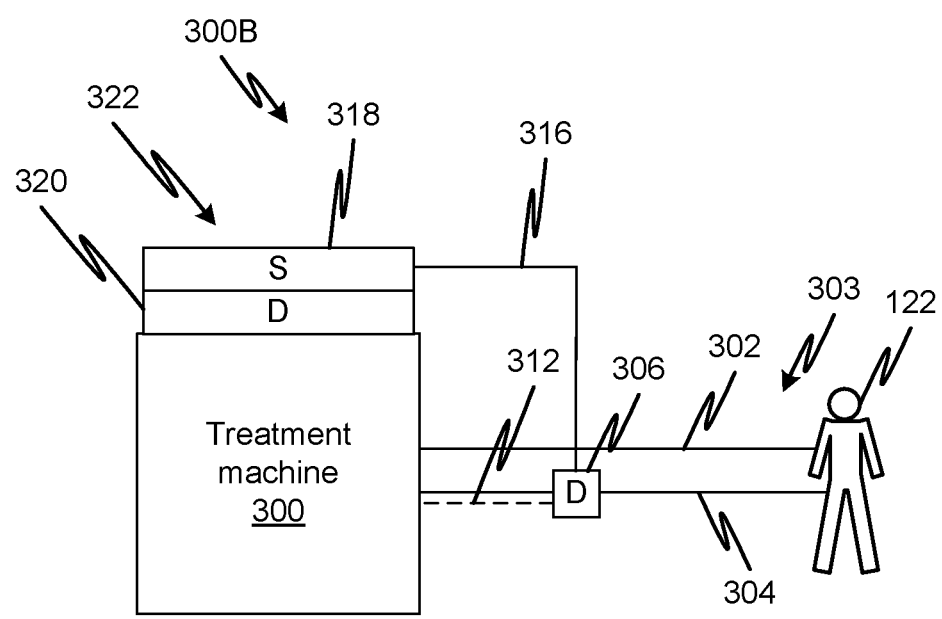

Any of the foregoing embodiments may include a mechanism for conditionally capturing fluid for further testing in response to an estimation, during a treatment, of a notable condition such as patient infection. FIGS. 5 and 6 show embodiments of systems 300A and 300B, respectively, that automatically divert a sample of fluid responsively to an estimation signal indicating an existing or possible condition of interest such as a patient infection. A treatment machine 300 may be a renal replacement therapy machine such as a hemodialysis, a hemofilter, a peritoneal dialysis machine, or any other type of machine for administration of medical treatments. Respective fluid circuits 301 or 303 include one or more lines including inlet and outlet lines 304 and 302, respectively. The treatment machine may include sensors and pumps (not shown) effective for providing and regulating a flow of fluid such as blood or peritoneal dialysate through the one or more lines. A flow diverter 306 is controlled by the treatment machine 300 as indicated by a dashed line 312. In the system 300A, a sample container 318 receives a sample of fluid in response to an estimate of a condition by the treatment machine 300. For example, the treatment machine (e.g., an internal controller on the treatment machine) may detect an infection as discussed above in response to a viscosity or temperature or other signals. In response, the flow diverter may be activated to generate a sample of fluid which is stored in the container 318. The flow diverter 306 may be combined in embodiments with the container 318. For example, the combination may be embodied in a syringe with a passive seal that is opened when the syringe is activated to draw a sample. The fluid may be blood, spent dialysate, or any other fluid described herein. In the system of FIG. 300B, the sample container 318 that receives the sample of fluid through a sample connection 316 is part of a fluid pack 322 which may include fresh dialysate concentrate or dry solute used for the preparation of dialysate 320.

FIG. 7A is a figurative illustration of the time-variation of a parameter 398 related to (preferably proportional) to viscosity of a spent peritoneal dialysate solution during a drain cycle of a cycler assisted treatment or other treatment. The parameter may be viscosity, proportional to viscosity or otherwise depend on viscosity, for example, pressure drop across a flow restriction. The flow restriction and pressure sensors may be structurally as identified with any of the disclosed embodiments, including blood circuit embodiments. The time-resolved signal may be samples from an A/D converter stored in a controller. The samples may represent a moving average or raw samples. The parameter may be derived from pressure signals. The pressure signals may be low-pass filtered (analog or digital). The parameter may be a sample or multiple samples at a predefined flow rate to minimize error when comparing samples taken at different times over a course of a drain cycle of a peritoneal dialysis treatment. The controller of the peritoneal dialysis cycler may convert the samples to a statistic and apply the statistic to an algorithm that indicates a potential of an infection. Examples of statistics may be the max value of the parameter, the average, a max value of a moving average defined by a selected averaging kernel, a measure of variability such as standard deviation or variance. Other statistics may be generated as well.

Because of a lack of mixing of the contents of the peritoneal cavity during the dwell phase, the viscosity of the spent dialysate residing at different regions of the peritoneal cavity such that as the spent dialysate is pumped out, corresponding variations in the time-resolved viscosity may appear. Even where there is little spatial variation in the viscosity of the spent fluid at the time of or just before draining, the maximum value and average statistics may reveal a magnitude of viscosity is indicative of infection. Thus, a controller may store threshold values for any of the statistics or others which may be compared to the statistic derived from the time-based parameter. A statistic whose value exceeds the threshold may cause the controller to generate a signal indicating a probability of an infection that is output by the controller. Multiple thresholds may be defined each corresponding to a probability as indicated by a table stored in the controller.

In response to the signal indicating a probability of an infection, the controller may output instructions for taking a sample of may automatically divert a sample to a container as taught in the present disclosure. Any of the other responses to a signal indicating a risk of infection discussed elsewhere herein may be taken by the controller, including outputting a message on a display of a user interface, storing an indication in a treatment log, reporting the result to a remote physician via a text message, email, telephone message or equivalent.

FIG. 7B is a figurative frequency domain signal derived from the time variation of a parameter related to (preferably proportional) to viscosity which may be based on a window function spanning seconds to minutes occur over a course of a drain cycle of a peritoneal dialysis treatment. The benefit of identifying a fluctuation in viscosity that may be revealed by such a filter (PSD stands for power spectral density in the figure), for example observing a peak 399 in a predefined frequency range, is that it can reveal inhomogeneous concentrations of thicker fluid or lumpiness in the spent peritoneal dialysate. While a similar capability may be attributed to a statistic based on the time-varying signal, such a filter may provide a more well-defined signature that is characteristic of certain infections. Of course, a pressure difference signal can be bans pass or high pass filtered to obtain a similar output.

FIG. 8 shows a metric of a parameter related to viscosity over multiple peritoneal dialysis treatments or multiple cycles of a single peritoneal dialysis treatment. Each bar 402, 404, 406 illustrates the value of the parameter, or a statistic thereof, for the given treatment of multiple treatments or for the different drain cycle of a single treatment. The controller may store these values with respect to time in order to identify any remarkable changes in the parameter in a given cycle relative to multiple cycles or for a given treatment of multiple treatments. The significant change (indicated by a change beyond a predefined threshold stored by the controller) may be used to identify a possible condition such as an infection of the peritoneum. Here then, the relative value of the parameter is the indicator rather than the absolute value alone. The relative change detection may be combined with the absolute value to provide an additional indicator. For example the threshold for a relative change may depend on the absolute magnitude of the parameter value.

In any of the foregoing and following embodiments, including the claims, where viscosity is identified as a parameter of interest, the viscosity may be replaced by a parameter that is related to it, for example proportional to viscosity with corresponding adjustments to any related thresholds. For example, rather than detecting viscosity, in any embodiment, a pressure difference may be detected and employed without further modification or reduction. It should be readily apparent that such embodiments may function in the same manner as described for embodiments where viscosity is directly detected or derived from a sensor signal such as a pressure difference signal. Also in any embodiment, including the claims, the parameter may be compared to predefined thresholds for a given flow rate or normalized against flow rate.

According to embodiments, the disclosed subject matter includes a fluid treatment system with a machine that has one or more pumps and a controller. The machine may include further actuators and sensors and may be adapted for administration of a medical treatment. A fluid circuit is in engagement with the one or more pumps and having inlet and outlet lines for conveying a fluid to and from a patient respectively. A viscosity sensor is present in at least the outlet line. The viscosity sensor generates a viscosity signal indicative of viscosity of fluid in the at least the outlet line. The controller is programmed to sample, at multiple times, the viscosity signal and store parameter data responsive thereto. The controller is further programmed to control the flow of fluid in the inlet and outlet lines responsively to the stored parameter data.

The embodiments further include variations of the foregoing embodiments in which the viscosity sensor in at least the outlet line is a viscosity sensor in the inlet and outlet lines. The embodiments further include variations of the foregoing embodiments in which the inlet line and outlet lines are blood lines. The embodiments further include variations of the foregoing embodiments in which the inlet line and outlet lines are peritoneal dialysate lines. The embodiments further include variations of the foregoing embodiments in which the inlet and outlet lines are blood lines connected to an inlet and outlet, respectively, of a treatment device.

The embodiments further include variations of the foregoing embodiments in which the machine is adapted to control a balance of fluid the patient by regulating a ratio of total volume of fluid removed from the patient to total volume supplied to the patient.

The embodiments further include variations of the foregoing embodiments in which the controller is programmed to estimate the ratio. The embodiments further include variations of the foregoing embodiments in which the controller is further programmed to estimate the ratio from the stored parameter data.

The embodiments further include variations of the foregoing embodiments in which the controller is further programmed to estimate the ratio independently of the stored parameter data. The embodiments further include variations of the foregoing embodiments in which the controller is further programmed to estimate the ratio from a signal indicating a pump speed, a fluid weight, a flow rate, or a fluid volume. The embodiments further include variations of the foregoing embodiments in which the controller calculates a patient fluid volume or rate of fluid volume loss from the parameter data.

The embodiments further include variations of the foregoing embodiments in which the controller calculates the patient fluid volume or rate of fluid volume loss from the parameter data, where the parameter data includes data responsive to viscosity and a predefined relationship between hematocrit and viscosity wherein the relationship is derived from historical data for the specific patient.

The embodiments further include variations of the foregoing embodiments in which the controller calculates a rate of fluid volume loss from the parameter data, the parameter data including hematocrit of blood entering and leaving the treatment device.

The embodiments further include variations of the foregoing embodiments in which the controller stores a function of hematocrit vs. viscosity and calculates hematocrit responsively to the function. The embodiments further include variations of the foregoing embodiments in which the function is a lookup table. The embodiments further include variations of the foregoing embodiments in which the viscosity sensors include pressure sensors upstream and downstream of a flow restriction. The embodiments further include variations of the foregoing embodiments in which the stored parameter is stored over multiple treatments for the patient to generate an historical record for the patient.

The embodiments further include variations of the foregoing embodiments in which the stored parameter over the multiple times is effective to indicate a trend over a course of treatment, the trend being stored over multiple treatments for the patient to generate an historical record of trends for the patient.

The embodiments further include variations of the foregoing embodiments in which the trends are stored as an average or a curve fit to viscosity over time to define a baseline trend which is compared by the controller to a current trend, and a result of the comparison output as a signal. The embodiments further include variations of the foregoing embodiments in which the controller is configured to output the parameter data to a treatment log. The embodiments further include variations of the foregoing embodiments in which the pressure sensors include pressure pods.

The embodiments further include variations of the foregoing embodiments in which the flow restriction is a length of tubing. The embodiments further include variations of the foregoing embodiments in which the viscosity sensor draws a sample of fluid from the fluid circuit and applies the sample to a viscometer. The embodiments further include variations of the foregoing embodiments in which the viscosity sensor draws a sample periodically throughout a treatment.

According to another main embodiment, the disclosed subject matter includes a fluid treatment system with a machine that has one or more pumps and a controller. A fluid circuit is in engagement with the one or more pumps and having inlet and outlet lines for conveying a fluid to and from a patient respectively. One or more fluid parameter sensors is present, at least one of which is in at least the outlet line. The one or more fluid property sensors generates a fluid property signal indicative of one or more properties of fluid in the at least the outlet line. The controller is programmed to sample, at multiple times, the fluid property signal and store parameter data responsive thereto. The controller is further programmed to one of, responsively to the stored parameter data, control the flow of fluid in the inlet and outlet lines or output an estimation of a condition of the machine or the patient and output data responsive to the estimation.

The embodiments further include variations of the foregoing embodiments in which the one or more fluid parameter sensors includes viscosity sensors in the inlet and outlet lines. The embodiments further include variations of the foregoing embodiments in which the inlet line and outlet lines are blood lines. The embodiments further include variations of the foregoing embodiments in which the inlet line and outlet lines are peritoneal dialysate lines.

The embodiments further include variations of the foregoing embodiments in which the inlet and outlet lines are blood lines connected to an inlet and outlet, respectively, of a treatment device. The embodiments further include variations of the foregoing embodiments in which the machine is adapted to control a balance of fluid the patient by regulating a ratio of total volume of fluid removed from the patient to total volume supplied to the patient.

The embodiments further include variations of the foregoing embodiments in which the controller is programmed to estimate the ratio independently of the parameter data. The embodiments further include variations of the foregoing embodiments in which the controller is further programmed to estimate the ratio from the stored parameter data. The embodiments further include variations of the foregoing embodiments in which the controller is further programmed to estimate the ratio independently of the stored parameter data.

The embodiments further include variations of the foregoing embodiments in which the controller is further programmed to estimate the ratio from a signal indicating a pump speed, a fluid weight, a flow rate, or a fluid volume. The embodiments further include variations of the foregoing embodiments in which the controller calculates a rate of fluid volume loss from the parameter data.

The embodiments further include variations of the foregoing embodiments in which the controller calculates the patient fluid volume or rate of fluid volume loss from the parameter data, where the parameter data includes data responsive to viscosity and a predefined relationship between hematocrit and viscosity wherein the relationship is derived from historical data for the specific patient.

The embodiments further include variations of the foregoing embodiments in which the controller stores a function of hematocrit vs. viscosity and calculates hematocrit responsively to the function. The embodiments further include variations of the foregoing embodiments in which the function is a lookup table. The embodiments further include variations of the foregoing embodiments in which the viscosity sensors include pressure sensors upstream and downstream of a flow restriction.

The embodiments further include variations of the foregoing embodiments in which the stored parameter is stored over multiple treatments for the patient to generate an historical record for the patient. The embodiments further include variations of the foregoing embodiments in which the stored parameter over the multiple times is effective to indicate a trend over a course of treatment, the trend being stored over multiple treatments for the patient to generate an historical record of trends for the patient.

The embodiments further include variations of the foregoing embodiments in which the trends are stored as an average or a curve fit to viscosity over time to define a baseline trend which is compared by the controller to a current trend. The embodiments further include variations of the foregoing embodiments in which the controller is configured to output the parameter data to a treatment log.

The embodiments further include variations of the foregoing embodiments in which the one or more fluid parameter sensors include a temperature sensor, a blood oximeter, an optical hematocrit sensor, a scale adapted for measuring the patient's weight, patient heart rate, galvanic skin resistance, and audio and/or video of a treatment area. The embodiments further include variations of the foregoing embodiments in which the controller is programmed to implement a classifier whose inputs include the fluid parameter signal and whose output is applied by the controller for display, control, or treatment log.

The embodiments further include variations of the foregoing embodiments in which the controller is programmed to implement a classifier whose inputs include the fluid parameter signal and whose output includes a signal indicating at least one of: a diagnosis including a patient infection and the patient's excess fluid level or weight above dry weight.

The embodiments further include variations of the foregoing embodiments in which the controller is programmed to automatically change or halt an ultrafiltration rate and record a series of the parameter data corresponding indicating a change in the fluid property over time. The embodiments further include variations of the foregoing embodiments in which the fluid circuit is a blood circuit and the series of parameter data indicates a change in fluid volume of blood.

The embodiments further include variations of the foregoing embodiments in which the controller is programmed to automatically change or halt an ultrafiltration rate and record a series of the parameter data corresponding indicating a change in the fluid property over one or more periods of time covering periods of different ultrafiltration rates. The embodiments further include variations of the foregoing embodiments in which the fluid circuit is a blood circuit and the series of parameter data indicates a change in fluid volume of blood.

According to yet another main embodiment, the disclosed subject matter includes a fluid treatment method that includes pumping fluid through a fluid circuit, the pumping conveying fluid to and from a patient for a medical treatment. The method includes detecting viscosity of the fluid from the patient. The method further includes sampling the viscosity detected in the detecting, at multiple times during a treatment, and storing parameter data responsive to viscosity samples resulting therefrom and controlling a flow of fluid in the fluid circuit responsively to the stored parameter data.

The embodiments further include variations of the foregoing embodiments in which the detecting includes detecting viscosity in fluid from the patient and fluid returned to the patient. The embodiments further include variations of the foregoing embodiments in which the fluid from the patient is blood.

The embodiments further include variations of the foregoing embodiments in which the fluid from the patient is spent peritoneal dialysate. The embodiments further include variations of the foregoing embodiments in which the fluid circuit conveys the fluid to a treatment device and returns it to the patient. The embodiments further include variations of the foregoing embodiments that include controlling a balance of fluid the patient by regulating a ratio of total volume of fluid removed from the patient to total volume supplied to the patient.

The embodiments further include variations of the foregoing embodiments that include estimating the ratio using a controller that controls the pumping. The embodiments further include variations of the foregoing embodiments that include using the controller estimating the ratio from the stored parameter data.

The embodiments further include variations of the foregoing embodiments that include using the controller estimating the ratio independently of the stored parameter data. The embodiments further include variations of the foregoing embodiments that include the controller to estimate the ratio from a signal indicating a pump speed, a fluid weight, a flow rate, or a fluid volume.

The embodiments further include variations of the foregoing embodiments that include, using the controller, calculating a rate of fluid volume loss from the parameter data. The embodiments further include variations of the foregoing embodiments that include, using the controller, calculating a rate of fluid volume loss from the parameter data, the parameter data including hematocrit of blood entering and leaving the treatment device.

The embodiments further include variations of the foregoing embodiments that include, using the controller, storing a function of hematocrit vs. viscosity and calculating hematocrit responsively to the function. The embodiments further include variations of the foregoing embodiments in which the function is a lookup table. The embodiments further include variations of the foregoing embodiments in which the detecting viscosity includes detecting pressure upstream and downstream of a flow restriction in the fluid circuit.

The embodiments further include variations of the foregoing embodiments in which the detecting viscosity includes detecting pressure upstream and downstream of a flow restriction in the fluid circuit. The embodiments further include variations of the foregoing embodiments in which the storing parameter data includes storing parameter data over multiple treatments for the patient to generate an historical record for the patient.

The embodiments further include variations of the foregoing embodiments in which the stored parameter is effective to indicate a trend over a course of treatment, the trend being stored over multiple treatments for the patient to generate an historical record of trends for the patient.

The embodiments further include variations of the foregoing embodiments in which the trends are stored as an average or a curve fit to viscosity over time to define a baseline trend which is compared by the controller to a current trend. The embodiments further include variations of the foregoing embodiments in which the controller is configured to output the parameter data to a treatment log. The embodiments further include variations of the foregoing embodiments in which the detecting pressure includes detecting pressure using a pressure pod.

The embodiments further include variations of the foregoing embodiments in which the flow restriction includes a length of tubing. The embodiments further include variations of the foregoing embodiments in which the detecting viscosity includes drawing a sample of fluid from the fluid circuit and applying the sample to a viscometer. The embodiments further include variations of the foregoing embodiments in which the detecting viscosity includes drawing a sample at regular intervals from the fluid circuit and applying the sample to a viscometer.

According to yet another embodiment, the disclosed subject matter includes a fluid treatment method that includes pumping fluid through a fluid circuit, the pumping conveying fluid to and from a patient for a medical treatment. The method further includes detecting one or more fluid properties of the fluid from a patient to generate a fluid property signal. The method further includes using a controller, sampling automatically at multiple times during a treatment, the fluid property signal and storing parameter data responsive thereto. The method further includes using the controller, responsively to the stored parameter data, controlling the flow of fluid in the inlet and outlet lines and outputting an estimation of a condition of the machine or the patient and output data responsive to the estimation.

The embodiments further include variations of the foregoing embodiments in which the one or more fluid parameters includes viscosity. The embodiments further include variations of the foregoing embodiments in which the fluid circuit includes blood lines and he fluid from the patient is blood. The embodiments further include variations of the foregoing embodiments in which the fluid from the patient is spent peritoneal dialysate.

The embodiments further include variations of the foregoing embodiments in which the fluid circuit conveys the fluid to a treatment device and returns it to the patient. The embodiments further include variations of the foregoing embodiments that include, controlling a balance of fluid the patient by regulating a ratio of total volume of fluid removed from the patient to total volume supplied to the patient.

The embodiments further include variations of the foregoing embodiments that include, estimating the ratio using a controller that controls the pumping. The embodiments further include variations of the foregoing embodiments that include, using the controller estimating the ratio from the stored parameter data. The embodiments further include variations of the foregoing embodiments that include, using the controller estimating the ratio independently of the stored parameter data.

The embodiments further include variations of the foregoing embodiments that include, the controller to estimate the ratio from a signal indicating a pump speed, a fluid weight, a flow rate, or a fluid volume. The embodiments further include variations of the foregoing embodiments that include, using the controller, calculating a rate of fluid volume loss from the parameter data. The embodiments further include variations of the foregoing embodiments that include, using the controller, calculating a rate of fluid volume loss from the parameter data, the parameter data including hematocrit of blood entering and leaving the treatment device. The embodiments further include variations of the foregoing embodiments that include, using the controller, storing a function of hematocrit vs. viscosity and calculating hematocrit responsively to the function.

The embodiments further include variations of the foregoing embodiments in which the function is a lookup table. The embodiments further include variations of the foregoing embodiments in which the detecting viscosity includes detecting pressure upstream and downstream of a flow restriction in the fluid circuit.

The embodiments further include variations of the foregoing embodiments in which the detecting viscosity includes detecting pressure upstream and downstream of a flow restriction in the fluid circuit. The embodiments further include variations of the foregoing embodiments in which the storing parameter data includes storing parameter data over multiple treatments for the patient to generate an historical record for the patient. The embodiments further include variations of the foregoing embodiments in which the stored parameter is effective to indicate a trend over a course of treatment, the trend being stored over multiple treatments for the patient to generate an historical record of trends for the patient.

The embodiments further include variations of the foregoing embodiments in which the trends are stored as an average or a curve fit to viscosity over time to define a baseline trend which is compared by the controller to a current trend. The embodiments further include variations of the foregoing embodiments in which the controller is configured to output the parameter data to a treatment log. The embodiments further include variations of the foregoing embodiments in which the detecting pressure includes detecting pressure using a pressure pod.

The embodiments further include variations of the foregoing embodiments in which the flow restriction includes a length of tubing. The embodiments further include variations of the foregoing embodiments in which the detecting viscosity includes drawing a sample of fluid from the fluid circuit and applying the sample to a viscometer.

The embodiments further include variations of the foregoing embodiments in which the detecting viscosity includes drawing a sample at regular intervals from the fluid circuit and applying the sample to a viscometer.

According to embodiments, the disclosed subject matter further includes a fluid treatment system with a fluid circuit having a control unit and a fluid line adapted for connection to a patient access. First and second pressure sensors are positioned along a flow path on either side of a flow restriction. The control unit is connected to receive samples of first and second pressure signals, respectively, from the first and second pressure sensors. The control unit is programmed to store the samples to generate at least one dynamic parameter associated with a property of a fluid flowing in the fluid line through the flow restriction. The samples being received and parameter data responsive thereto stored, during a treatment, the at least one dynamic parameter being generated responsively to the parameter data. The control unit has a data store that stores at least one predicted parameter that corresponds to an acceptable range of the dynamic parameter. The control unit programmed further to classify at least one condition of a current treatment or at least one condition of a current patient responsively to said at least one dynamic parameter and said at least one predicted parameter.

The embodiments further include variations of the foregoing embodiments in which the at least one dynamic parameter includes a curve-fit to a time series obtained from the samples and the predicted parameter includes a definition of a curve, the control unit comparing the definition with the curve-fit to classify the at least one condition. The embodiments further include variations of the foregoing embodiments in which the at least one stored parameter includes a curve-fit to a time series obtained from the samples from prior treatments.

The embodiments further include variations of the foregoing embodiments in which the at least one stored parameter includes a curve-fit to a time series obtained from the samples from prior treatments of a unique patient. The embodiments further include variations of the foregoing embodiments in which the at least one stored parameter includes a curve-fit to a time series obtained from the samples from prior treatments.

The embodiments further include variations of the foregoing embodiments in which the at least one stored parameter includes a curve-fit to a time series obtained from the samples from prior treatments of a unique patient. The embodiments further include variations of the foregoing embodiments in which the at least one stored parameter includes a curve-fit to a time series obtained from the samples from prior peritoneal dialysis treatments of a unique class of patients. The embodiments further include variations of the foregoing embodiments in which the at least one stored parameter includes a curve-fit to a time series obtained from the samples from prior peritoneal dialysis treatments of multiple patients.

The embodiments further include variations of the foregoing embodiments in which the at least one stored parameter includes a patient model. The embodiments further include variations of the foregoing embodiments in which the at least one stored parameter includes a patient model, the patient model including parameters of an individual patient. The embodiments further include variations of the foregoing embodiments in which the parameters of an individual patient include metrics related to obesity.

The embodiments further include variations of the foregoing embodiments in which the parameters of an individual patient include metrics related to a rate of recruitment of factors that affect patient temperature, heat, and viscosity of a fluid from the patient's body.

According to further embodiments, the disclosed subject matter includes a blood treatment system with a blood circuit. The system has a control unit and a blood line adapted for connection to a patient access. First and second pressure sensors are positioned along a flow path on either side of a flow restriction. The control unit is connected to receive samples of first and second pressure signals, respectively, from the first and second pressure sensors. The control unit is programmed to store the samples to generate at least one dynamic parameter associated with a property of a blood flowing in the blood line through the flow restriction. The samples are received and stored, during a treatment, the at least one dynamic parameter being generated responsively to multiple ones of the samples. The control unit has a data store that stores at least one predicted parameter that corresponds to an acceptable range of the dynamic parameter. The control unit is programmed further to classify at least one condition of a current treatment or at least one condition of a current patient responsively to the at least one dynamic parameter and the at least one predicted parameter.

The embodiments further include variations of the foregoing embodiments in which the at least one dynamic parameter includes a curve-fit to a time series obtained from the samples and the predicted parameter includes a definition of a curve, the control unit comparing the definition with the curve-fit to classify the at least one condition.

The embodiments further include variations of the foregoing embodiments in which the at least one stored parameter includes a curve-fit to a time series obtained from the samples from prior treatments. The embodiments further include variations of the foregoing embodiments in which the at least one stored parameter includes a curve-fit to a time series obtained from the samples from prior treatments of a unique patient. The embodiments further include variations of the foregoing embodiments in which the at least one stored parameter includes a curve-fit to a time series obtained from the samples from prior treatments.

The embodiments further include variations of the foregoing embodiments in which the at least one stored parameter includes a curve-fit to a time series obtained from the samples from prior treatments of a unique patient. The embodiments further include variations of the foregoing embodiments in which the at least one stored parameter includes a patient model. The embodiments further include variations of the foregoing embodiments in which the at least one stored parameter includes a patient model, the patient model including parameters of an individual patient.

The embodiments further include variations of the foregoing embodiments in which the parameters of an individual patient include metrics related to obesity. The embodiments further include variations of the foregoing embodiments in which the parameters of an individual patient include metrics related to a rate of recruitment of factors that affect patient temperature, heat, and viscosity of a blood from the patient's body.

According to further embodiments, the disclosed subject matter includes a method of treating a patient using a fluid treatment system. The method includes using a fluid circuit with a control unit and a fluid line adapted for connection to a patient access. The fluid circuit has first and second pressure sensors positioned along a flow path on either side of a flow restriction. The control unit is connected to receive samples of first and second pressure signals, respectively, from the first and second pressure sensors. The method further includes using the control unit, storing the samples to generate at least one dynamic parameter, associated with a property of a fluid flowing in the fluid line through the flow restriction. The method further includes receiving the samples being received and stored, during a treatment, the at least one dynamic parameter being generated responsively to multiple ones of the samples. The method further includes using the control unit, storing at least one predicted parameter that corresponds to an acceptable range of the dynamic parameter in a data store of the control unit. The method further includes using the control unit, classifying at least one condition of a current treatment or at least one condition of a current patient responsively to the at least one dynamic parameter and the at least one predicted parameter.

The embodiments further include variations of the foregoing embodiments in which the at least one dynamic parameter includes a curve-fit to a time series obtained from the samples and the predicted parameter includes a definition of a curve, the control unit comparing the definition with the curve-fit to classify the at least one condition.

The embodiments further include variations of the foregoing embodiments in which the at least one stored parameter includes a curve-fit to a time series obtained from the samples from prior treatments. The embodiments further include variations of the foregoing embodiments in which the at least one stored parameter includes a curve-fit to a time series obtained from the samples from prior treatments of a unique patient. The embodiments further include variations of the foregoing embodiments in which the at least one stored parameter includes a curve-fit to a time series obtained from the samples from prior treatments.

The embodiments further include variations of the foregoing embodiments in which the at least one stored parameter includes a curve-fit to a time series obtained from the samples from prior treatments of a unique patient. The embodiments further include variations of the foregoing embodiments in which the at least one stored parameter includes a curve-fit to a time series obtained from the samples from prior peritoneal dialysis treatments of a unique class of patients.

The embodiments further include variations of the foregoing embodiments in which the at least one stored parameter includes a curve-fit to a time series obtained from the samples from prior peritoneal dialysis treatments of multiple patients. The embodiments further include variations of the foregoing embodiments in which the at least one stored parameter includes a patient model.

The embodiments further include variations of the foregoing embodiments in which the at least one stored parameter includes a patient model, the patient model including parameters of an individual patient. The embodiments further include variations of the foregoing embodiments in which the parameters of an individual patient include metrics related to obesity.

The embodiments further include variations of the foregoing embodiments in which the parameters of an individual patient include metrics related to a rate of recruitment of factors that affect patient temperature, heat, and viscosity of a fluid from the patient's body. The embodiments further include variations of any of the foregoing systems or methods where a patient condition is estimated by the controller responsively to a combination of two or more of heart rate, hematocrit, blood oxygen, patient weight, galvanic skin resistance, blood or spent peritoneal dialysate viscosity, and blood temperature, as detected by a respective sensor and applied to the controller and a responsive signal generated by the controller.

The embodiments further include variations of the foregoing embodiments in which the controller is programmed to implement a classifier to estimate the condition where the classifier has inputs include the combination and outputs the responsive signal for display, control, or treatment logging. The embodiments further include variations of the foregoing embodiments in which the condition includes an infection of the patient.

Embodiments of the disclosed subject matter include any combination or subcombination of the limitations of the following dependent claims, that depend from a common independent claim, with the limitations of that common independent claim.

Further embodiments include any of the following claims that recite a viscosity-dependent parameter, where the viscosity-dependent parameter includes a pressure drop indicated by detecting the pressure different across a blood circuit element.

It will be appreciated that the modules, processes, systems, and sections described above can be implemented in hardware, hardware programmed by software, software instruction stored on a non-transitory computer readable medium or a combination of the above. For example, a method for determining a patient or treatment condition can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#, .net, or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to, read-only memory (ROM), programmable read-only memory (PROM), electrically erasable programmable read-only memory (EEPROM), random-access memory (RAM), flash memory, disk drive, and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), a programmable logic array (PLA), a field-programmable gate array (FPGA), a programmable array logic (PAL) device, or the like. In general, any process capable of implementing the functions or steps described herein can be used to implement embodiments of a method, a system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control and measurement systems, machine-assisted diagnosis, and/or computer programming arts.

Moreover, embodiments of the disclosed method, system, and computer program product can be implemented in software executed on a programmed general-purpose computer, a special purpose computer, a microprocessor, or the like.

The foregoing descriptions apply, in some cases, to examples generated in a laboratory, but these examples can be extended to production techniques. For example, where quantities and techniques apply to the laboratory examples, they should not be understood as limiting.

Features of the disclosed embodiments may be combined, rearranged, omitted, etc., within the scope of the invention to produce additional embodiments. Furthermore, certain features may sometimes be used to advantage without a corresponding use of other features.

Figure 9:
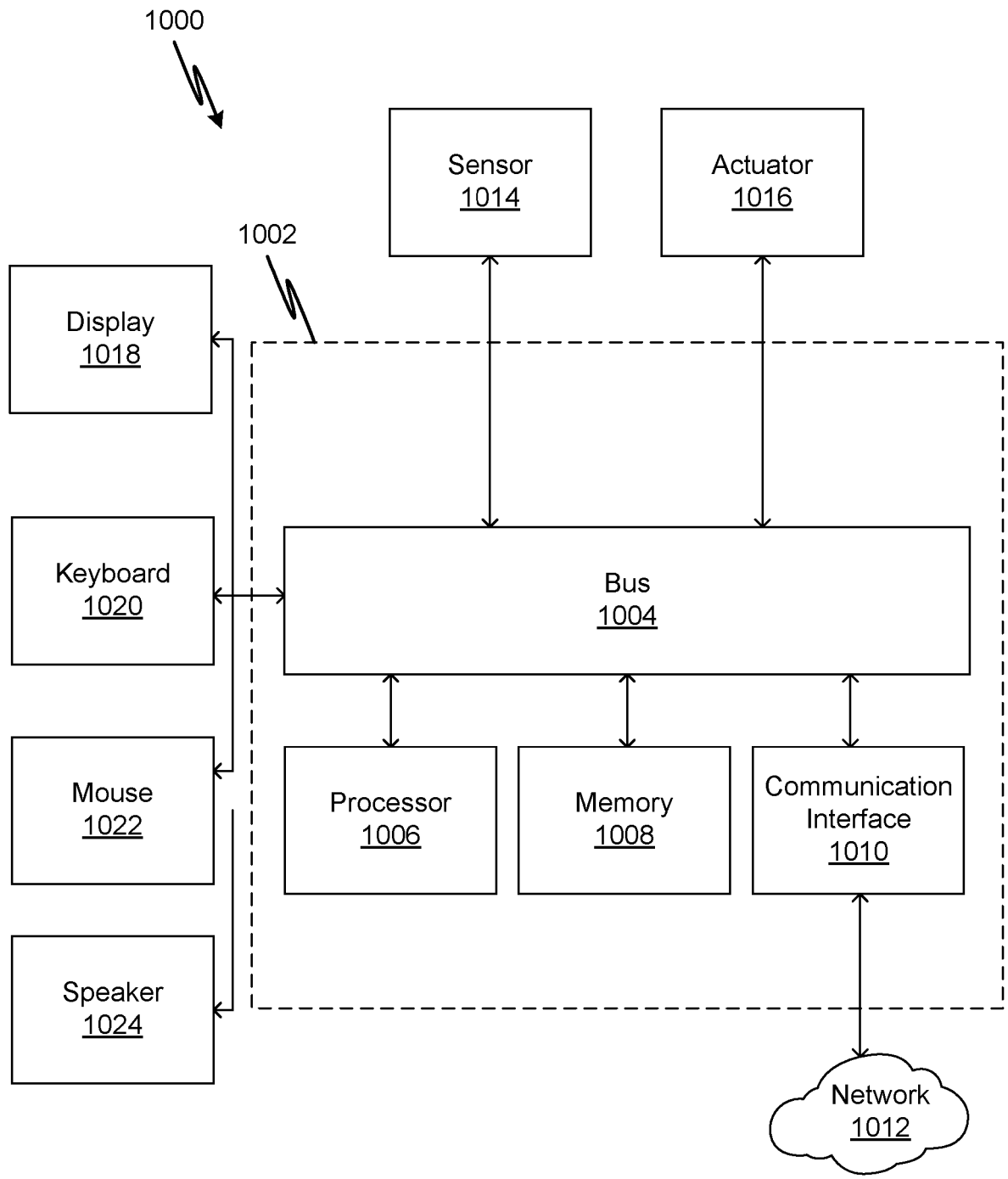
FIG. 9 is a block diagram of an example computer system according to embodiments of the disclosed subject matter.

FIG. 9 is a block diagram of an example computer system 1000 according to an embodiment. In various embodiments, all or parts of system 1000 may be included in a medical treatment device/system such as a renal replacement therapy system. In these embodiments, all or parts of system 1000 may provide the functionality of a controller of the medical treatment device/systems. In some embodiments, all or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In embodiments, such instructions may be compiled from source code/objects provided in accordance with a programming language such as Java, C++, C#, .net, Visual Basic™, LabVIEW, or another structured or object-oriented programming language. In embodiments, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a treatment for a patient and monitoring a patient during a treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with a sensor 1014 and/or an actuator 1016, each providing respective functionality in accordance with various embodiments disclosed herein, for example, for measuring signals indicative of a patient/device condition and for controlling the operation of the device accordingly. For example, sensor 1014 may provide a signal indicative of a viscosity of a fluid in a fluid circuit in a renal replacement therapy device, and actuator 1016 may operate a pump that controls the flow of the fluid responsively to the signals of sensor 1014.

It is, thus, apparent that there is provided, in accordance with the present disclosure, diagnosis based on viscosity changes in treatment systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A blood treatment system, comprising:
a machine comprising one or more pumps;
a blood circuit in engagement with the one or more pumps and having an inlet line for conveying blood to a patient and an outlet line for conveying the blood from the patient;
a treatment device configured to treat the blood and having a first port and a second port, the first port of the treatment device fluidly connected to the inlet line and the second port of the treatment device fluidly connected to the outlet line;
at least one of the inlet line or the outlet line having at least two pressure sensors positioned in it and a flow restriction located between said at least two pressure sensors, wherein all of the at least two pressure sensors are disposed upstream or downstream from a pump, among the one or more pumps, said pump being disposed in a same one of the inlet and outlet lines as the at least two pressure sensors; and
a controller configured to control the one or more pumps to convey blood to and from the patient, the controller further configured to use readings of the at least two pressure sensors to determine a change over time in a pressure drop across the flow restriction and to perform an action responsive to the change in the pressure drop, the action comprising at least one of:

generating a notification, adjusting a blood flow rate in the blood circuit, outputting an estimation of a condition of the machine or the patient, or outputting data responsive to said estimation.

2. The blood treatment system of claim 1, wherein the controller is configured to sample the pressure drop at multiple times over a period of time comprising a single treatment or multiple treatments and store data responsive thereto, wherein the change in the pressure drop is determined based on a trend over time of the stored data.

3. The blood treatment system of claim 2, wherein the controller, responsively to said trend, generates a user notification, caution, or alarm, indicating that the trend is exceeding a limit.

4. The blood treatment system of claim 2, wherein the inlet line comprises an arterial line and the outlet line comprises a venous line.

5. The blood treatment system of claim 2, wherein the machine is adapted to control a balance of fluid in the patient by regulating a ratio of a total volume of fluid removed from the patient to a total volume of fluid supplied to the patient.

6. The blood treatment system of claim 5, wherein the controller is programmed to estimate said ratio from said stored data.

7. The blood treatment system of claim 5, wherein the controller is programmed to estimate said ratio independently of said stored data by using a signal indicating a pump speed, a fluid weight, a flow rate, or a fluid volume.

8. The blood treatment system of claim 2, wherein the controller calculates a rate of fluid volume loss from said stored data.

9. The blood treatment system of claim 8, wherein a relationship between viscosity and hematocrit is derived from historical data for the patient or for a class of patients into which the patient belongs.

10. The blood treatment system of claim 8, wherein the controller stores a function of hematocrit versus viscosity-dependent parameter or hemoglobin versus viscosity, wherein the controller calculates hematocrit or hemoglobin responsively to said function and responsively to the stored data and wherein the controller outputs said hematocrit or hemoglobin.

11. The blood treatment system of claim 10, wherein the function is a lookup table.

12. The blood treatment system of claim 2, wherein the at least two pressure sensors include two pressure sensors upstream and two pressure sensors downstream of the flow restriction.

13. The blood treatment system of claim 2, wherein the stored data is stored over multiple treatments for said patient to generate a historical record for said patient.

14. The blood treatment system of claim 13, wherein the stored data over said multiple treatments indicates a trend over a course of therapy, said trend being stored over the multiple treatments for said patient to generate a historical record of trends for said patient.

15. The blood treatment system of claim 14, wherein the trends are stored as an average or a curve fit to viscosity over time to provide a baseline trend, wherein the baseline trend is compared by said controller to a current trend, and a result of the comparison is output as a signal.

16. The blood treatment system of claim 2, wherein the controller is configured to output said stored data to a treatment log.

17. The blood treatment system of claim 1, wherein the at least two pressure sensors include pressure pods.

18. The blood treatment system of claim 1, wherein the flow restriction in a flow path includes a physical structure in the flow path that causes a pressure drop between an inlet of the flow path and an outlet of the flow path.

19. The blood treatment system of claim 18, wherein the physical structure is a reduction of tubing diameter compared to the inlet and the outlet of the flow path.

20. The blood treatment system of claim 1, further comprising a viscosity sensor, wherein the viscosity sensor draws a sample of blood from said blood circuit and applies the sample to a viscometer.

21. A blood treatment system, comprising:

a machine comprising one or more pumps;

a blood circuit in engagement with the one or more pumps and having a venous line for conveying blood to a patient and an arterial line for conveying the blood from the patient;

a treatment device configured to treat the blood and having an inlet port and an outlet port, the inlet port of the treatment device fluidly connected to the arterial line and the outlet port of the treatment device fluidly connected to the venous line;

at least two pressure sensors in the venous line or in the arterial line, with two pressure sensors of the at least two pressure sensors being in a same line and a flow restriction that causes a pressure drop from upstream to downstream of the flow restriction; and a controller configured to control the one or more pumps to convey blood to and from the patient, the controller further configured to use readings of the at least two pressure sensors to determine a change over time in a pressure drop across the flow restriction and to perform an action responsive to the change in the pressure drop, the action comprising at least one of:

generating a notification, adjusting a blood flow rate in the blood circuit, outputting an estimation of a condition of the machine or the patient, or outputting data responsive to said estimation, wherein the controller is configured to sample the pressure drop at multiple times over a period of time comprising a single treatment or multiple treatments and store data responsive thereto, wherein the change in the pressure drop is determined based on a trend over time of the stored data.

22. The blood treatment system of claim 21, wherein the flow restriction in a flow path includes a reduction of tubing diameter compared to an inlet and an outlet of the flow path.

23. The blood treatment system of claim 21, wherein both of the two pressure sensors are disposed upstream or downstream from a pump, among the one or more pumps, said pump being disposed in the same line with the two pressure sensors.

* * * * *